US008337718B2

(12) United States Patent
Goto et al.

(10) Patent No.: US 8,337,718 B2
(45) Date of Patent: Dec. 25, 2012

(54) LIQUID CRYSTAL COMPOUND, LIQUID CRYSTAL COMPOSITION AND LIQUID CRYSTAL DISPLAY DEVICE

(75) Inventors: Shuichi Goto, Minamata (JP); Kouki Sagou, Ichihara (JP); Hiroaki Fujita, Ichihara (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 118 days.

(21) Appl. No.: 13/012,678

(22) Filed: Jan. 24, 2011

(65) Prior Publication Data
US 2011/0180756 A1   Jul. 28, 2011

(30) Foreign Application Priority Data

Jan. 27, 2010  (JP) ................................. 2010-015041

(51) Int. Cl.
C09K 19/00   (2006.01)
C09K 19/06   (2006.01)
C09K 19/32   (2006.01)
C09K 19/52   (2006.01)

(52) U.S. Cl. ........... 252/299.6; 252/299.01; 252/299.61; 252/299.63; 252/299.64; 252/299.65; 428/1.1; 428/1.3; 349/1; 349/56; 349/182

(58) Field of Classification Search ........................ None
See application file for complete search history.

(56) References Cited

U.S. PATENT DOCUMENTS
7,842,358 B2 * 11/2010 Czanta et al. .................. 428/1.1

FOREIGN PATENT DOCUMENTS
JP   2001-003053 A   9/2001

* cited by examiner

Primary Examiner — Geraldina Visconti
(74) Attorney, Agent, or Firm — Hogan Lovells US LLP

(57) ABSTRACT

The subject is to provide a liquid crystal composition that satisfies at least one of characteristics such as a high maximum temperature of a nematic phase, a low minimum temperature of a nematic phase, a small viscosity, a suitable optical anisotropy, a large dielectric anisotropy, a large specific resistance, a high stability to ultraviolet light, a high stability to heat and a large elastic constant, or that is suitably balanced regarding at least two of the characteristics. The subject is to provide an AM device that has a short response time, a large voltage holding ratio, a large contrast ratio, a long service life and so forth. The invention provides a liquid crystal composition that has a nematic phase and includes a specific four-ring compound having a high maximum temperature and a large dielectric anisotropy as a first component and a specific compound having a small dielectric anisotropy as a second component, and also provides a liquid crystal display device containing this composition. The invention further provides the compound of the first component.

10 Claims, No Drawings

LIQUID CRYSTAL COMPOUND, LIQUID CRYSTAL COMPOSITION AND LIQUID CRYSTAL DISPLAY DEVICE

This nonprovisional application claims priority under 35 U.S.C. §119(a) on Patent Application No. 2010-015041 filed in Japan on Jan. 27, 2010, the entire contents of which are hereby incorporated by reference.

BACKGROUND OF THE INVENTION

1. Field of the Invention

The invention relates mainly to a liquid crystal composition suitable for use in an active matrix (AM) device, and an AM device containing the composition. More specifically, the invention relates to a liquid crystal composition having a positive dielectric anisotropy, and a device containing the composition and having a mode such as twisted nematic, optically compensated bend, in-plane switching, fringe field switching or polymer sustained alignment.

2. Related Art

In a liquid crystal display device, a classification based on an operating mode for liquid crystals includes phase change (PC), twisted nematic (TN), super twisted nematic (STN), electrically controlled birefringence (ECB), optically compensated bend (OCB), in-plane switching (IPS), vertical alignment (VA), fringe field switching (FFS) and polymer sustained alignment (PSA). A classification based on a driving mode in the device includes a passive matrix (PM) and an active matrix (AM). The PM is further classified into static, multiplex and so forth, and the AM is classified into a thin film transistor (TFT), a metal-insulator-metal (MIM) and so forth. The TFT is further classified into amorphous silicon and polycrystal silicon. The latter is classified into a high temperature type and a low temperature type according to the production process. A classification based on a light source includes a reflection type utilizing natural light, a transmission type utilizing a backlight and a semi-transmission type utilizing both natural light and a backlight.

These devices contain a liquid crystal composition having suitable characteristics. The liquid crystal composition has a nematic phase. General characteristics of the composition should be improved to give an AM device having excellent general characteristics. Table 1 below summarizes the relationship between the general characteristics of the two. The general characteristics of the composition will be explained further based on a commercially available AM device. The temperature range of a nematic phase relates to the temperature range in which the device can be used. A desirable maximum temperature of the nematic phase is approximately 70° C. or higher and a desirable minimum temperature of the nematic phase is approximately −10° C. or lower. The viscosity of the composition relates to the response time of the device. A short response time is desirable for displaying moving images on the device. Accordingly, a small viscosity of the composition is desirable. A small viscosity at a low temperature is more desirable. The elastic constant of the composition relates to the contrast of the device. A large elastic constant of the composition is more desirable in order to increase the contrast of the device.

TABLE 1

General Characteristics of Composition and AM Device

| No. | General Characteristics of Composition | General Characteristics of AM Device |
|---|---|---|
| 1 | wide temperature range of a nematic phase | wide usable temperature range |
| 2 | small viscosity[1] | short response time |
| 3 | suitable optical anisotropy | large contrast ratio |
| 4 | positively or negatively large dielectric anisotropy | low threshold voltage and small electric power consumption large contrast ratio |
| 5 | large specific resistance | large voltage holding ratio and large contrast ratio |
| 6 | high stability to ultraviolet light and heat | long service life |
| 7 | large elastic constant | large contrast ratio and short response time |

[1] A liquid crystal composition can be injected into a liquid crystal cell in a shorter period of time.

The optical anisotropy of the composition relates to the contrast ratio of the device. The product ($\Delta n \times d$) of the optical anisotropy ($\Delta n$) of the composition and the cell gap (d) of the device is designed so as to maximize the contrast ratio. A suitable value of the product depends on the kinds of operating modes. In a device having a TN mode, a suitable value is about 0.45 micrometer. In this case, a composition having a large optical anisotropy is desirable for a device having a small cell gap. A large dielectric anisotropy of the composition contributes to a low threshold voltage, a small electric power consumption and a large contrast ratio of the device. Accordingly, a large dielectric anisotropy is desirable. A large specific resistance of the composition contributes to a large voltage holding ratio and a large contrast ratio of the device. Accordingly, a composition having a large specific resistance is desirable at room temperature and also at a temperature close to the maximum temperature of a nematic phase in the initial stage. A composition having a large specific resistance is desirable at room temperature and also at a temperature close to the maximum temperature of a nematic phase after it has been used for a long time. The stability of the composition to ultraviolet light and heat relates to the service life of the liquid crystal display device. In the case where the stability is high, the device has a long service life. These characteristics are desirable for an AM device used in a liquid crystal projector, a liquid crystal television and so forth. A large elastic constant of the composition relates to a large contrast ratio and a short response time of the device. Accordingly, a large elastic constant is desirable.

A composition having positive dielectric anisotropy is used for an AM device having a TN mode. On the other hand, a composition having negative dielectric anisotropy is used for an AM device having a VA mode. A composition having positive or negative dielectric anisotropy is used for an AM device having an IPS mode or a FFS mode. A composition having positive or negative dielectric anisotropy is used for an AM device having a PSA mode. Liquid crystal compositions having positive dielectric anisotropy are disclosed in the patent document No. 1. Patent document No. 1: JP 2001-003053 A.

A desirable AM device has characteristics such as a wide temperature range in which the device can be used, a short response time, a large contrast ratio, a low threshold voltage, a large voltage holding ratio and a long service life. Response time that is one millisecond shorter than that of the other devices is desirable. Thus, a composition having characteristics such as a high maximum temperature of a nematic phase, a low minimum temperature of a nematic phase, a small viscosity, a suitable optical anisotropy, a large dielectric anisotropy, a large specific resistance, a high stability to ultraviolet light and a high stability to heat is especially desirable.

SUMMARY OF THE INVENTION

The invention concerns a liquid crystal composition that has a nematic phase and includes two components, wherein a first component is at least one compound selected from the group of compounds represented by formula (1), and a second component is at least one compound selected from the group of compounds represented by formula (2), and concerns also a liquid crystal display device containing this composition:

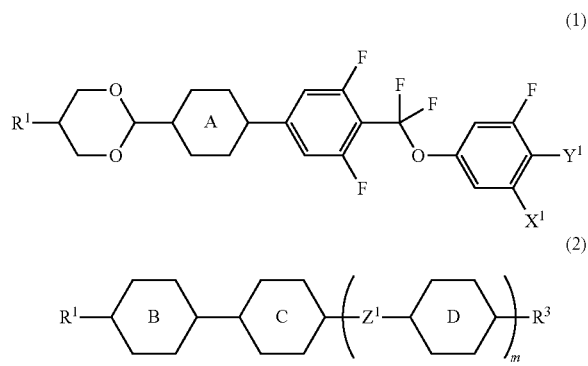

wherein $R^1$ is alkyl having 1 to 12 carbons or alkenyl having 2 to 12 carbons; $R^2$ is alkyl having 1 to 12 carbons, alkenyl having 2 to 12 carbons, or alkenyl having 2 to 12 carbons in which hydrogen is replaced by fluorine; $R^3$ is alkyl having 1 to 12 carbons, alkoxy having 1 to 12 carbons, alkoxymethyl having 2 to 12 carbons or alkenyl having 2 to 12 carbons; the ring A, the ring B, the ring C and the ring D are each independently 1,4-cyclohexylene, 1,4-phenylene, 2-fluoro-1,4-phenylene, 3-fluoro-1,4-phenylene, 3,5-difluoro-1,4-phenylene, 2,5-difluoro-1,4-phenylene or tetrahydropyran-2,5-diyl; $X^1$ is hydrogen or fluorine; $Y^1$ is fluorine, chlorine or trifluoromethoxy; $Z^1$ is independently a single bond, ethylene or carbonyloxy; and m is 0, 1 or 2.

The invention also concerns the compound of the first component.

DETAILED DESCRIPTION OF THE INVENTION

The terms used in the specification and claims are defined as follows. The liquid crystal composition and the liquid crystal display device of the invention may occasionally be abbreviated to "the composition" and "the device," respectively. "A liquid crystal display device" is a generic term for a liquid crystal display panel and a liquid crystal display module. "A liquid crystal compound" is a generic term for a compound having a liquid crystal phase such as a nematic phase and a smectic phase, and also for a compound having no liquid crystal phases but being useful as a component of a composition. Such a compound has a six-membered ring such as 1,4-cyclohexylene and 1,4-phenylene, and a rod-like molecular structure. An optically active compound and a polymerizable compound may occasionally be added to the composition. Even in the case where these compounds are liquid crystalline, the compounds are classified as an additive herein. At least one compound selected from the group of compounds represented by formula (1) may occasionally be abbreviated to "the compound (1)." "The compound (1)" means one compound, or two or more compounds represented by formula (1). The same rules apply to compounds represented by the other formulas. "Arbitrary hydrogen" means that not only the position of hydrogen but also its number may be selected without specific restriction.

A higher limit of the temperature range of a nematic phase may occasionally be abbreviated to "the maximum temperature." A lower limit of the temperature range of a nematic phase may occasionally be abbreviated to "the minimum temperature." That "specific resistance is large" means that a composition has a large specific resistance at room temperature and also at a temperature close to the maximum temperature of a nematic phase in the initial stage, and that the composition has a large specific resistance at room temperature and also at a temperature close to the maximum temperature of a nematic phase even after it has been used for a long time. That "a voltage holding ratio is large" means that a device has a large voltage holding ratio at room temperature and also at a temperature close to the maximum temperature of a nematic phase in the initial stage, and that the device has a large voltage holding ratio at room temperature and also at a temperature close to the maximum temperature of a nematic phase even after it has been used for along time. When characteristics such as optical anisotropy are explained, values which are obtained according to the measuring methods described in Examples will be used. A first component means one compound, or two or more compounds. "The ratio of the first component" is expressed as a percentage by weight (% by weight) of the first component based on the total weight of the liquid crystal composition. The same rule applies to the ratio of a second component and so forth. The ratio of an additive mixed with the composition is expressed as a percentage by weight (% by weight) or weight parts per million (ppm) based on the total weight of the liquid crystal composition.

The symbol $R^1$ is used for a plurality of compounds in the chemical formulas of component compounds. In these compound, arbitrary two $R^1$ selected arbitrary may be the same groups or different groups. In one case, for example, $R^1$ of the compound (1) is ethyl and $R^1$ of the compound (1-1) is ethyl. In another case, $R^1$ of the compound (1) is ethyl and $R^1$ of the compound (1-1) is propyl. The same rule applies to the symbols $X^1$, $Y^1$ and so forth.

One of the advantages of the invention is to provide a liquid crystal composition that satisfies at least one of characteristics such as a high maximum temperature of a nematic phase, a low minimum temperature of a nematic phase, a small viscosity, a suitable optical anisotropy, a large dielectric anisotropy, a large specific resistance, a high stability to ultraviolet light, a high stability to heat and a large elastic constant. Another advantage of the invention is to provide a liquid crystal composition that is suitably balanced regarding at least two of the characteristics. A further advantage of the invention is to provide a liquid crystal display device that contains such a composition. An additional advantage of the invention is to provide a liquid crystal composition that has characteristics such as a suitable optical anisotropy, a large dielectric anisotropy, a high stability to ultraviolet light and a large elastic constant, and is to provide an AM device that has characteristics such as a short response time, a large voltage holding ratio, a large contrast ratio and a long service life.

The liquid crystal composition of the invention satisfied at least one of characteristics such as a high maximum temperature of a nematic phase, a low minimum temperature of a nematic phase, a small viscosity, a suitable optical anisotropy, a large dielectric anisotropy, a large specific resistance, a high stability to ultraviolet light, a high stability to heat and a large elastic constant. The liquid crystal composition was suitably balanced regarding at least two of the characteristics. The liquid crystal display device contained such a composition.

The liquid crystal composition had characteristics such as a suitable optical anisotropy, a large dielectric anisotropy, a high stability to ultraviolet light and a large elastic constant, and the AM device had characteristics such as a short response time, a large voltage holding ratio, a large contrast ratio and a long service life.

The invention includes the following items. Item 1. A liquid crystal composition that has a nematic phase and includes two components, wherein a first component is at least one compound selected from the group of compounds represented by formula (1), and a second component is at least one compound selected from the group of compounds represented by formula (2):

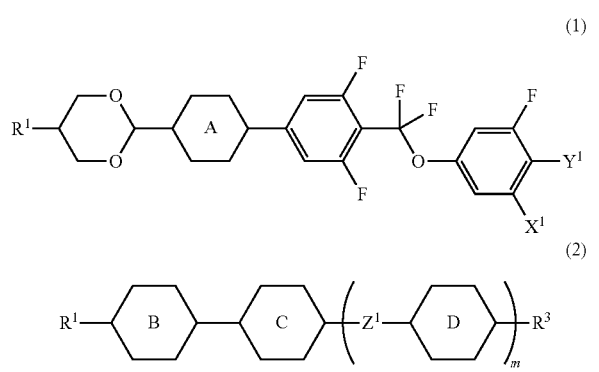

wherein $R^1$ is alkyl having 1 to 12 carbons or alkenyl having 2 to 12 carbons; $R^2$ is alkyl having 1 to 12 carbons, alkenyl having 2 to 12 carbons, or alkenyl having 2 to 12 carbons in which hydrogen is replaced by fluorine; $R^3$ is alkyl having 1 to 12 carbons, alkoxy having 1 to 12 carbons, alkoxymethyl having 2 to 12 carbons or alkenyl having 2 to 12 carbons; the ring A, the ring B, the ring C and the ring D are each independently 1,4-cyclohexylene, 1,4-phenylene, 2-fluoro-1,4-phenylene, 3-fluoro-1,4-phenylene, 3,5-difluoro-1,4-phenylene, 2,5-difluoro-1,4-phenylene or tetrahydropyran-2,5-diyl; $X^1$ is hydrogen or fluorine; $Y^1$ is fluorine, chlorine or trifluoromethoxy; $Z^1$ is independently a single bond, ethylene or carbonyloxy; and m is 0, 1 or 2.

Item 2. The liquid crystal composition according to item 1, wherein the ratio of the first component is in the range of approximately 5% to approximately 30% by weight and the ratio of the second component is in the range of approximately 5% to approximately 40% by weight, based on the total weight of the liquid crystal composition.

Item 3. The liquid crystal composition according to item 1, further including at least one compound selected from the group of compounds represented by formula (3-1) to formula (3-3) as a third component:

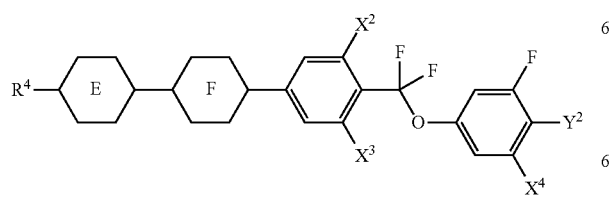

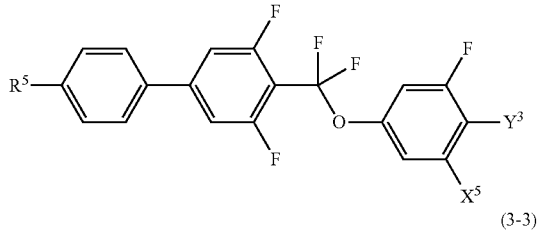

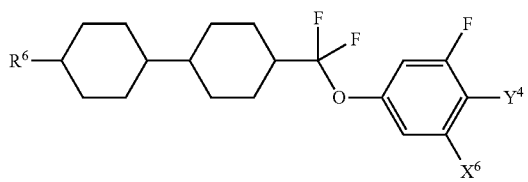

wherein $R^4$, $R^5$ and $R^6$ are each independently alkyl having 1 to 12 carbons or alkenyl having 2 to 12 carbons; the ring E is 1,4-cyclohexylene, 1,4-phenylene, 2-fluoro-1,4-phenylene, 3-fluoro-1,4-phenylene, 3,5-difluoro-1,4-phenylene or tetrahydropyran-2,5-diyl; the ring F is 1,4-cyclohexylene, 1,4-phenylene, 2-fluoro-1,4-phenylene, 3-fluoro-1,4-phenylene, 3,5-difluoro-1,4-phenylene, 1,3-dioxane-2,5-diyl or tetrahydropyran-2,5-diyl; $X^2$, $X^3$, $X^4$, $X^5$ and $X^6$ are each independently hydrogen or fluorine; and $Y^2$, $Y^3$ and $Y^4$ are each independently fluorine, chlorine or trifluoromethoxy.

Item 4. The liquid crystal composition according to item 3, wherein the ratio of the first component is in the range of approximately 5% to approximately 30% by weight, the ratio of the second component is in the range of approximately 5% to approximately 40% by weight, and the ratio of the third component is in the range of approximately 5% to approximately 70% by weight, based on the total weight of the liquid crystal composition.

Item 5. The liquid crystal composition according to item 1 or 3, further including at least one compound selected from the group of compounds represented by formula (4) as a fourth component:

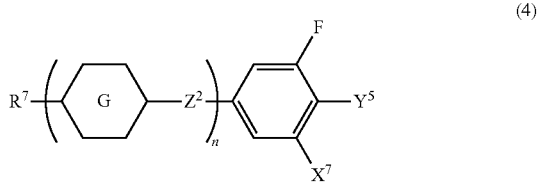

wherein $R^7$ is alkyl having 1 to 12 carbons or alkenyl having 2 to 12 carbons; the ring G is independently 1,4-cyclohexylene, 1,4-phenylene, 2-fluoro-1,4-phenylene, 3-fluoro-1,4-phenylene, 3,5-difluoro-1,4-phenylene, 1,3-dioxane-2,5-diyl or tetrahydropyran-2,5-diyl; $X^7$ is hydrogen or fluorine; $Y^5$ is fluorine, chlorine or trifluoromethoxy; $Z^2$ is independently a single bond, ethylene or carbonyloxy; and n is 1, 2 or 3.

Item 6. The liquid crystal composition according to item 5, wherein the ratio of the first component is in the range of approximately 5% to approximately 30% by weight, the ratio of the second component is in the range of approximately 5% to approximately 40% by weight, the ratio of the third component is in the range of 0% to approximately 60% by weight, and the ratio of the fourth component is in the range of approximately 5% to approximately 50% by weight based on the total weight of the liquid crystal composition.

Item 7. The liquid crystal composition according to any one of items 1 to 6, wherein the first component is at least one compound selected from the group of compounds represented by formula (1-1-1), formula (1-2-1) and formula (1-3-1):

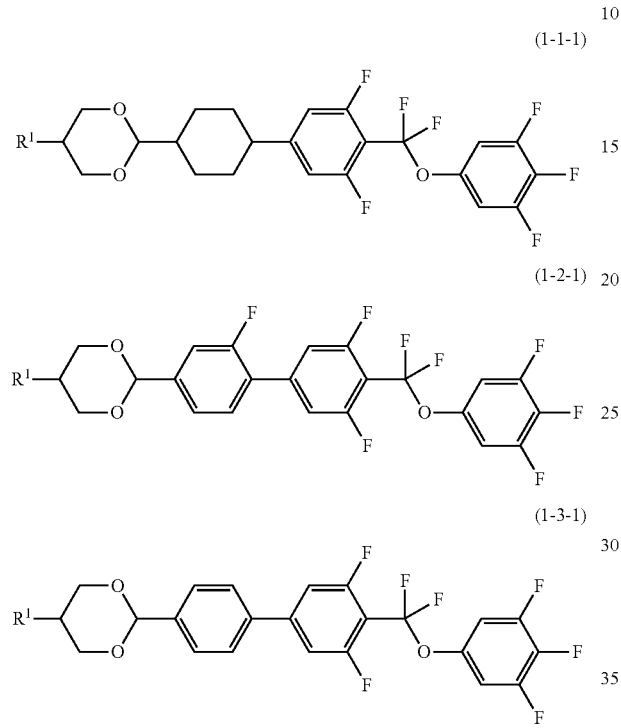

(1-1-1)

(1-2-1)

(1-3-1)

wherein $R^1$ is alkyl having 1 to 12 carbons or alkenyl having 2 to 12 carbons.

Item 8. The liquid crystal composition according to any one of items 1 to 7, wherein the second component is at least one compound selected from the group of compounds represented by formula (2-1) to formula (2-15):

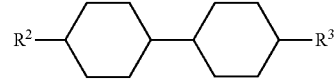

(2-1)

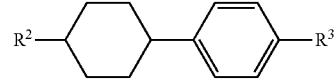

(2-2)

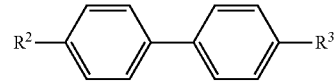

(2-3)

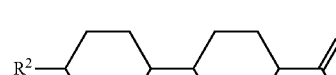

(2-4)

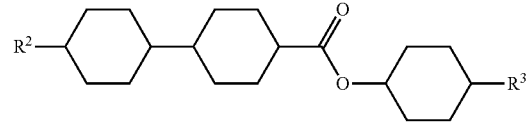

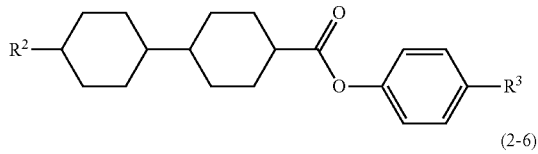

(2-5)

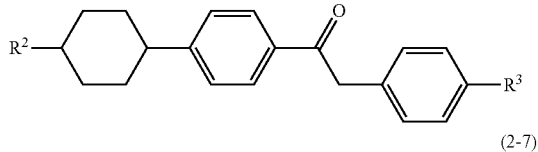

(2-6)

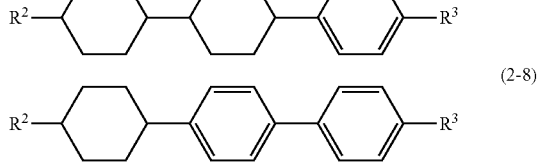

(2-7)

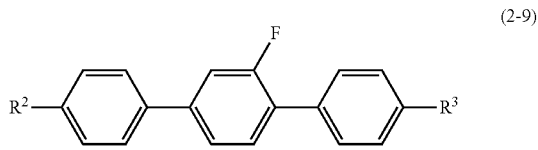

(2-8)

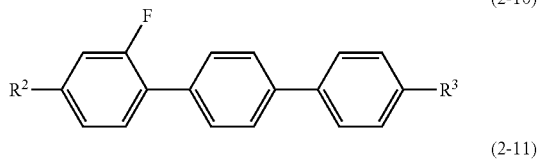

(2-9)

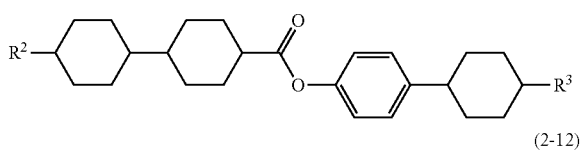

(2-10)

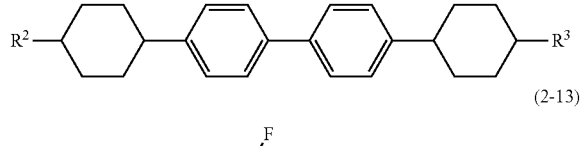

(2-11)

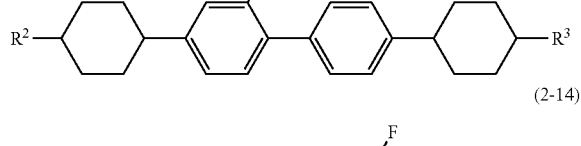

(2-12)

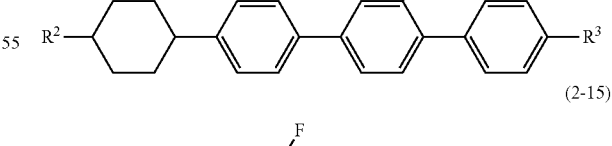

(2-13)

(2-14)

(2-15)

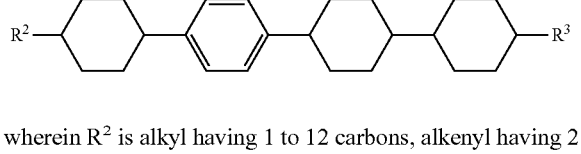

wherein $R^2$ is alkyl having 1 to 12 carbons, alkenyl having 2 to 12 carbons, or alkenyl having 2 to 12 carbons in which hydrogen is replaced by fluorine; and $R^3$ is alkyl having 1 to 12 carbons, alkoxy having 1 to 12 carbons, alkoxymethyl having 2 to 12 carbons or alkenyl having 2 to 12 carbons.

Item 9. The liquid crystal composition according to item 8, wherein the second component is at least one compound selected from the group of compounds represented formula (2-1), formula (2-7), formula (2-9) and formula (2-14).

Item 10. The liquid crystal composition according to any one of items 1 to 7, wherein the second component is at least one compound selected from the group of compounds represented by formula (2-1):

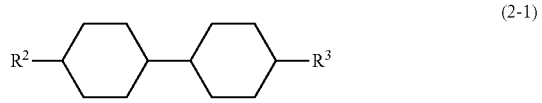
(2-1)

wherein $R^2$ is alkyl having 1 to 12 carbons, alkenyl having 2 to 12 carbons, or alkenyl having 2 to 12 carbons in which hydrogen is replaced by fluorine; and $R^3$ is alkyl having 1 to 12 carbons, alkoxy having 1 to 12 carbons, alkoxymethyl having 2 to 12 carbons or alkenyl having 2 to 12 carbons.

Item 11. The liquid crystal composition according to any one of items 3 to 5, and items 7 to 10, wherein the third component is at least one compound selected from the group of compounds represented by formula (3-1-1) to formula (3-1-7), formula (3-2-1) and formula (3-3-1):

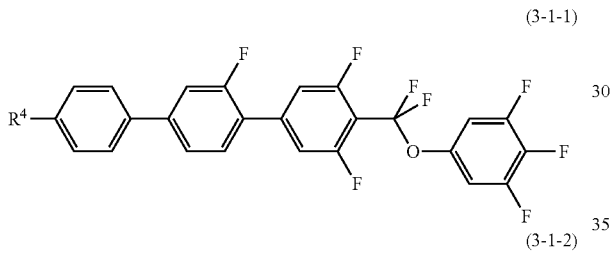
(3-1-1)

(3-1-2)

(3-1-3)

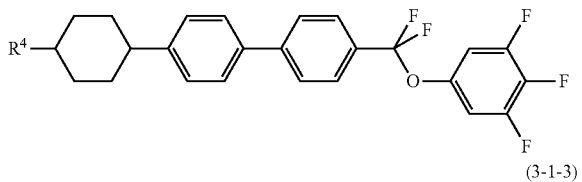
(3-1-4)

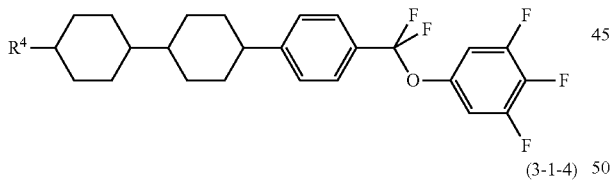
(3-1-5)

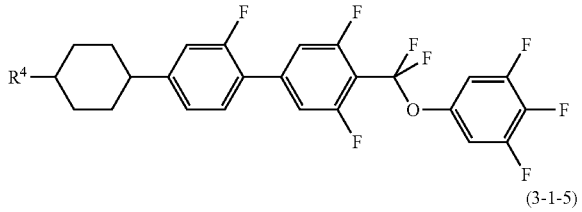

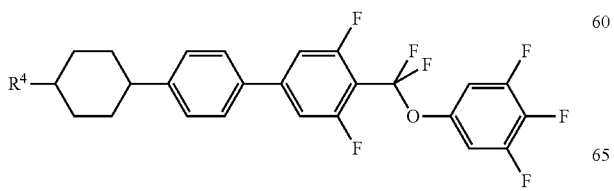

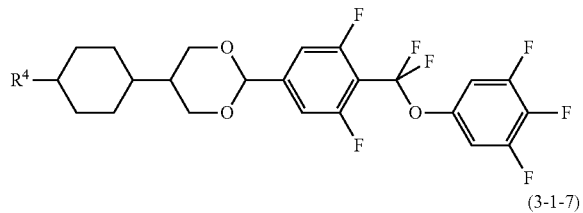
(3-1-6)

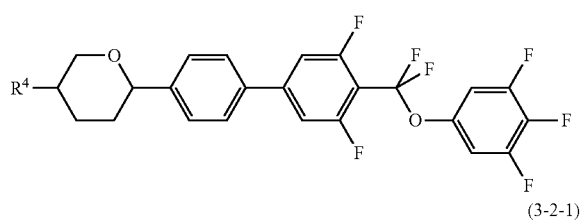
(3-1-7)

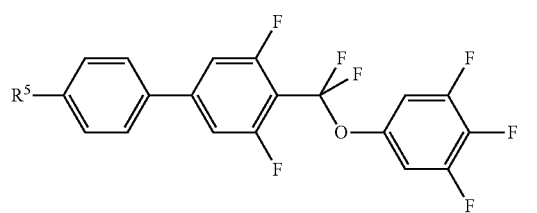
(3-2-1)

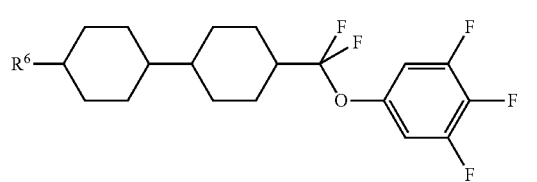
(3-3-1)

wherein $R^4$, $R^5$ and $R^6$ are each independently alkyl having 1 to 12 carbons or alkenyl having 2 to 12 carbons.

Item 12. The liquid crystal composition according to any one of items 3 to 11, wherein the third component is at least one compound selected from the group of compounds represented by formula (3-1-1) to formula (3-1-3), formula (3-2-1) and formula (3-3-1):

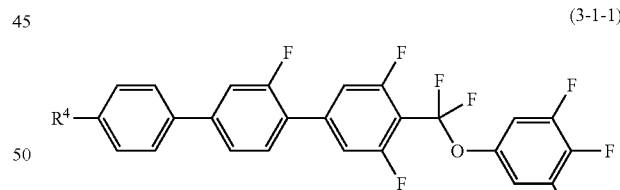
(3-1-1)

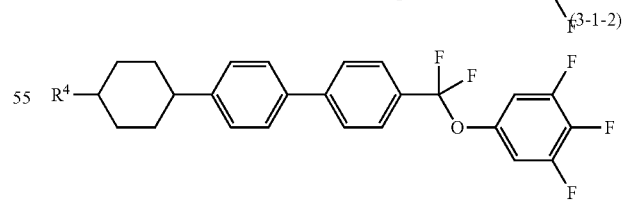
(3-1-2)

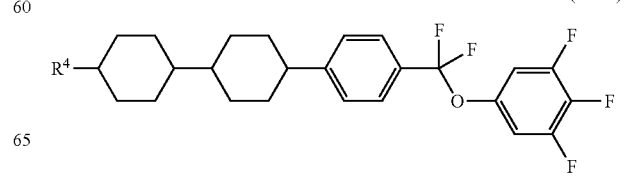
(3-1-3)

(3-2-1)

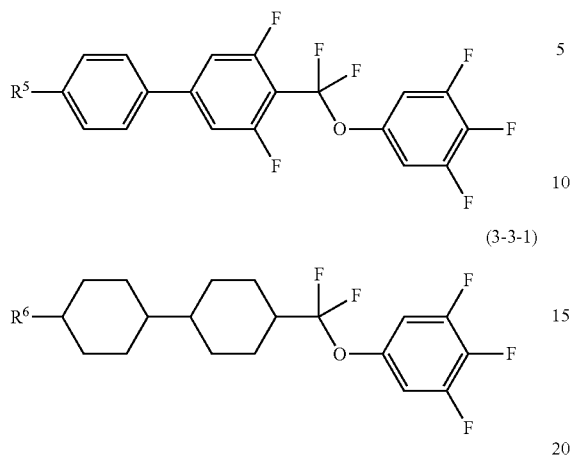

(3-3-1)

wherein $R^4$, $R^5$ and $R^6$ are each independently alkyl having 1 to 12 carbons or alkenyl having 2 to 12 carbons.

Item 13. The liquid crystal composition according to item 11, wherein the third component is at least one compound selected from the group of compounds represented by formula (3-1-1) to formula (3-1-6).

Item 14. The liquid crystal composition according to item 11, wherein the third component is at least one compound selected from the group of compounds represented by formula (3-1-1) to formula (3-1-3).

Item 15. The liquid crystal composition according to item 11, wherein the third component is at least one compound selected from the group of compounds represented by formula (3-1-1).

Item 16. The liquid crystal composition according to any one of items 5 to 15, wherein the fourth component is at least one compound selected from the group of compounds represented by formula (4-1) to formula (4-16):

(4-1)

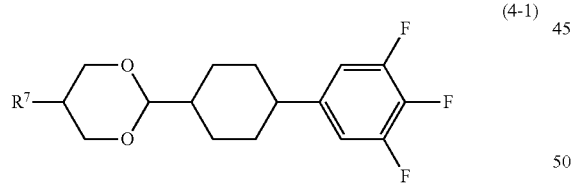

(4-2)

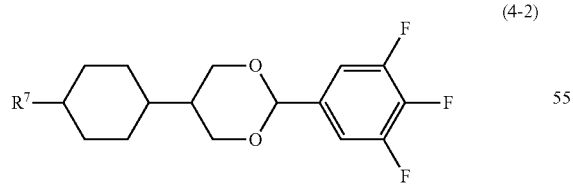

(4-3)

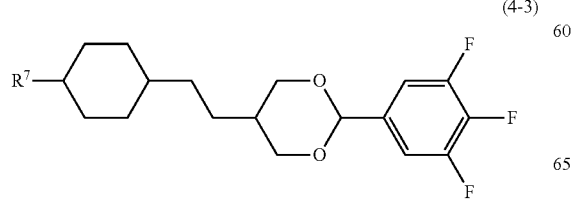

(4-4)

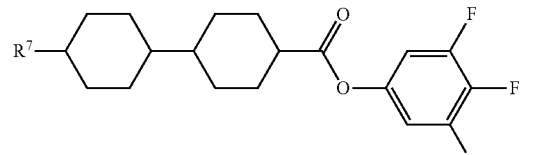

(4-5)

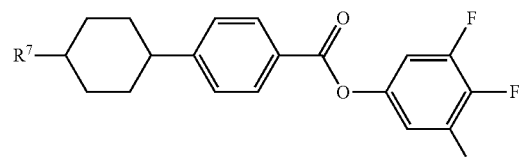

(4-6)

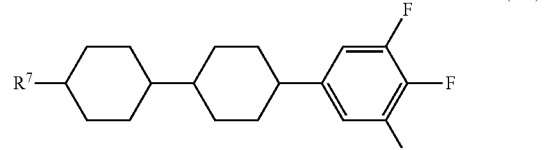

(4-7)

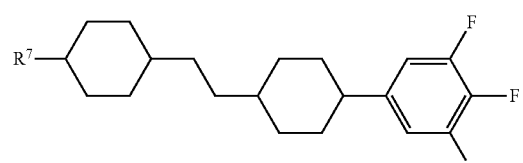

(4-8)

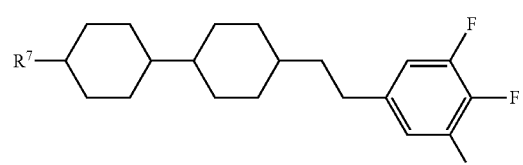

(4-9)

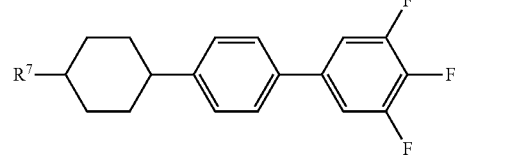

(4-10)

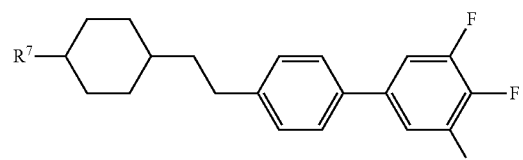

(4-11)

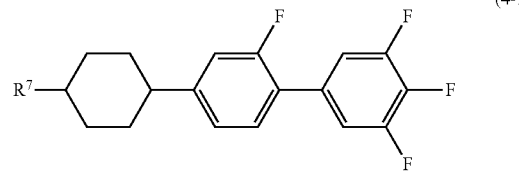

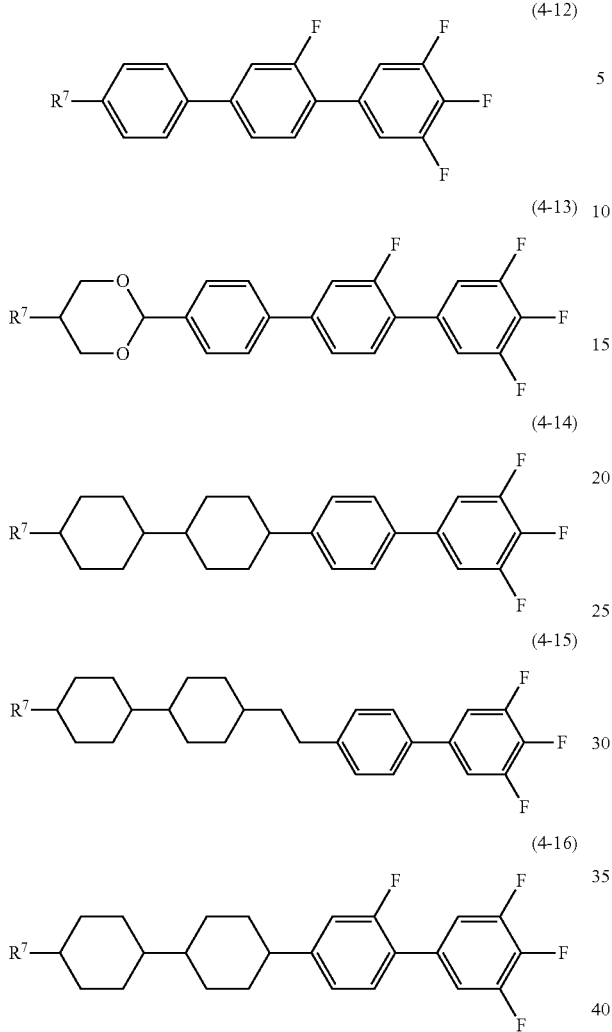
wherein R⁷ is alkyl having 1 to 12 carbons or alkenyl having 2 to 12 carbons.
Item 17. The liquid crystal composition according to any one of items 5 to 16, wherein the fourth component is at least one compound selected from the group of compounds represented by formula (4-1) to formula (4-11):
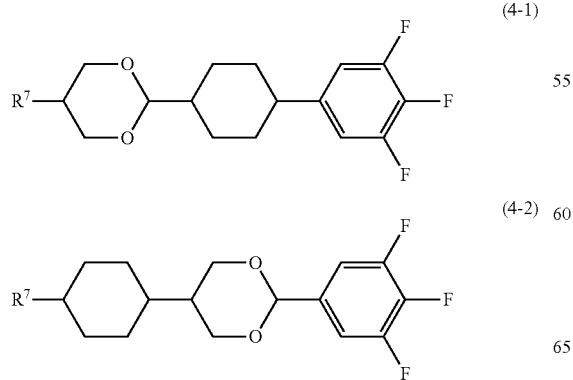

(4-11)

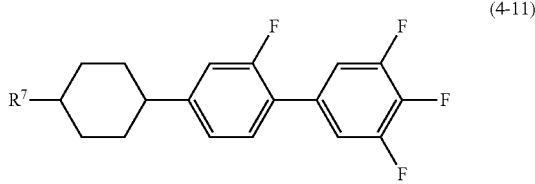

wherein R⁷ is alkyl having 1 to 12 carbons or alkenyl having 2 to 12 carbons.

Item 18. The liquid crystal composition according to any one of items 5 to 16, wherein the fourth component is at least one compound selected from the group of compounds represented by formula (4-1) to formula (4-5).

Item 19. The liquid crystal composition according to any one of items 5 to 18, wherein the first component is at least one compound selected from the group of compounds represented by formula (1-1-1) to formula (1-3-1), the second component is at least one compound selected from the group of compounds represented by formula (2-1), formula (2-7), formula (2-9) and formula (2-14), the third component is at least one compound selected from the group of compounds represented by formula (3-1-1) to formula (3-1-6), formula (3-2-1) and formula (3-3-1), and the fourth component is at least one compound selected from the group of compounds represented by formula (4-1) to formula (4-11).

Item 20. The liquid crystal composition according to any one of items 5 to 18, wherein the first component is at least one compound selected from the group of compounds represented by formula (1-2-1), the second component is at least one compound selected from the group of compounds represented by formula (2-1), the third component is at least one compound selected from the group of compounds represented by formula (3-1-1), formula (3-1-6), formula (3-2-1) and formula (3-3-1), and the fourth component is at least one compound selected from the group of compounds represented by formula (4-1) to formula (4-5).

Item 21. The liquid crystal composition according to any one of items 5 to 20, wherein the ratio of the first component is in the range of approximately 5% to approximately 30% by weight, the ratio of the second component is in the range of approximately 5% to approximately 40% by weight, the ratio of the third component is in the range of approximately 10% to approximately 60% by weight, and the ratio of the fourth component is in the range of approximately 5% to approximately 50% by weight, based on the total weight of the liquid crystal composition.

Item 22. A compound represented by formula (1-1):

(1-1)

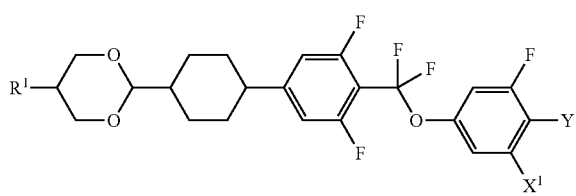

wherein R¹ is alkyl having 1 to 12 carbons or alkenyl having 2 to 12 carbons; X¹ is hydrogen or fluorine; and Y¹ is fluorine, chlorine or trifluoromethoxy.

Item 23. A compound represented by formula (1-2):

(1-2)

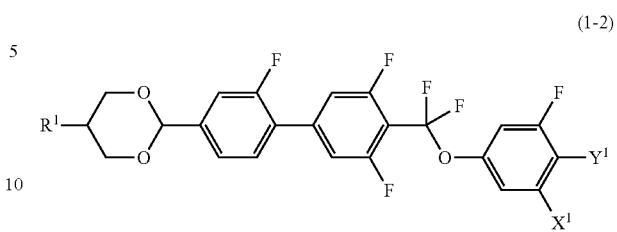

wherein R¹ is alkyl having 1 to 12 carbons or alkenyl having 2 to 12 carbons; X¹ is hydrogen or fluorine; and Y¹ is fluorine, chlorine or trifluoromethoxy.

Item 24. A liquid crystal display device containing the liquid crystal composition according to any one of items 1 to 21, or a liquid crystal composition including the compound according to item 22 or 23.

Item 25. The liquid crystal display device according to item 24, wherein an operating mode of the liquid crystal display device is a TN mode, an OCB mode, an IPS mode, a FFS mode or a PSA mode, and a driving mode of the liquid crystal display device is an active matrix mode.

Item 26. The liquid crystal composition according to any one of items 1 to 21, wherein the dielectric anisotropy (25° C.) at a frequency of 1 kHz is approximately 17 or more.

The invention further includes the following items: (1) the composition described above that further includes an optically active compound; (2) the composition described above that further includes an additive, such as an antioxidant, an ultraviolet light absorbent, an antifoaming agent, a polymerizable compound and/or a polymerization initiator; (3) an AM device that contains the composition described above; (4) a device that has a mode of TN, ECB, OCB, IPS, FFS or PSA and contains the composition described above; (5) a device that has a transmission type and includes the composition described above; (6) use of the composition described above as a composition having a nematic phase; and (7) use as an optically active composition by adding an optically active compound to the composition described above.

The composition of the invention will be explained in the following order. First, the constitution of component compounds in the composition will be explained. Second, main characteristics of the component compounds and main effects of the component compounds on the characteristics of the composition will be explained. Third, a combination of components in the composition, desirable ratios of the components and the basis thereof will be explained. Fourth, a desirable embodiment of the component compounds will be explained. Fifth, examples of the component compounds will be shown. Sixth, additives that may be mixed with the composition will be explained. Seventh, methods for synthesizing the component compounds will be explained. Last, use of the composition will be explained.

First, the constitution of component compounds in the composition will be explained. The compositions of the invention are classified into the composition A and the composition B. In addition to the compound (1), the compound (2), the compound (3-1) to the compound (3-3) and the compound (4), the composition A may include any other liquid crystal compound, an additive and an impurity. "Any other liquid crystal compound" is different from the compound (1), the compound (2), the compound (3-1) to the compound (3-3) and the compound (4). Such a compound is mixed with the composition for the purpose of further adjusting characteristics of the composition. The additive includes an optically active compound, an antioxidant, an ultraviolet light absorbent, a coloring matter, an antifoaming agent, a polymerizable compound and a polymerization initiator. The impurity is a compound and so forth which contaminated component compounds in a process such as their synthesis. Even in the case where the compound is liquid crystalline, it is classified into an impurity herein.

The composition B consists essentially of compounds selected from the group of the compound (1), the compound (2), the compound (3-1) to the compound (3-3) and the compound (4). The term "essentially" means that the composition may include an additive and an impurity, but does not include any liquid crystal compound other than these component compounds. The composition B has a smaller number of components than the composition A. The composition B is preferable to the composition A in view of cost reduction. The composition A is preferable to the composition B in view of the fact that characteristics can be further adjusted by adding any other liquid crystal compound.

Second, main characteristics of the component compounds and main effects of the component compounds on the characteristics of the composition will be explained. The main characteristics of the component compounds are summarized in Table 2 on the basis of the effects of the invention. In Table 2, the symbol L stands for "large" or "high", the symbol M stands for "medium", and the symbol S stands for "small" or "low." The symbols L, M and S are classified on the basis of a qualitative comparison among the component compounds, and 0 (zero) means that "a value is nearly zero."

TABLE 2

| Characteristics of Compounds | | | | | | |
|---|---|---|---|---|---|---|
| | Compounds | | | | | |
| | (1) | (2) | (3-1) | (3-2) | (3-3) | (4) |
| Maximum Temperature | L | S-L | L | S | M | S-L |
| Viscosity | L | S-M | L | M | M | L |
| Optical Anisotropy | M | S-L | M-L | M | M | S-M |
| Dielectric Anisotropy | L | 0 | L | L | L | M-L |
| Specific Resistance | L | L | L | L | L | L |

Main effects of the component compounds on the characteristics of the composition upon mixing the component compounds with the composition are as follows. The compound (1) increases the maximum temperature and greatly increases the dielectric anisotropy. The compound (2) decreases the minimum temperature and decreases the viscosity. The compound (3-1) increases the maximum temperature and greatly increases the dielectric anisotropy. The compound (3-2) greatly increases the dielectric anisotropy although it decreases the maximum temperature. The compound (3-3) greatly increases the dielectric anisotropy. The compound (4) decreases the minimum temperature and increases the dielectric anisotropy.

Third, a combination of components in the composition, desirable ratios of the components and the basis thereof will be explained. The combinations of the components in the composition is the first and second components, the first, second and third components, the first, second and fourth components, and the first, second, third and fourth components. A desirable combination of the components in the composition is the first, second and third components, and the first, second, third and fourth components for increasing the dielectric anisotropy, for decreasing the viscosity, and for decreasing the minimum temperature.

A desirable ratio of the first component is approximately 5% by weight or more for increasing the dielectric anisotropy, and is approximately 30% by weight or less for decreasing the minimum temperature. A more desirable ratio is in the range of approximately 5% to approximately 20% by weight. An especially desirable ratio is in the range of approximately 5% to approximately 10% by weight.

A desirable ratio of the second component is approximately 5% by weight or more for decreasing the viscosity, and is approximately 40% by weight or less for increasing the dielectric anisotropy. A more desirable ratio is in the range of approximately 5% to approximately 30% by weight. An especially desirable ratio is in the range of approximately 5% to approximately 25% by weight.

The third component is suitable for the preparation of a composition having a large dielectric anisotropy. A desirable ratio of the third component is approximately 5% by weight or more for increasing the dielectric anisotropy, and is approximately 70% by weight or less for decreasing the minimum temperature. A more desirable ratio is in the range of approximately 10% to approximately 60% by weight. An especially desirable ratio is in the range of approximately 20% to approximately 50% by weight.

The fourth component is suitable for the preparation of a composition having a large dielectric anisotropy. A desirable ratio of the fourth component is in the range of approximately 5% to approximately 50% by weight. A more desirable ratio is in the range of approximately 10% to approximately 40% by weight. An especially desirable ratio is in the range of approximately 15% to approximately 35% by weight.

Fourth, a desirable embodiment of the component compounds will be explained. $R^1$, $R^4$, $R^5$, $R^6$ and $R^7$ are each independently alkyl having 1 to 12 carbons or alkenyl having 2 to 12 carbons. Desirable $R^1$, $R^4$, $R^5$, $R^6$ or $R^7$ is alkyl having 1 to 12 carbons for increasing the stability to ultraviolet light or for increasing the stability to heat. More desirable $R^1$, $R^4$, $R^5$, $R^6$ or $R^7$ is alkyl having 1 to 5 carbons for decreasing the viscosity or for increasing the elastic constant. $R^2$ is alkyl having 1 to 12 carbons, alkenyl having 2 to 12 carbons, or alkenyl having 2 to 12 carbons in which hydrogen is replaced by fluorine. Desirable $R^2$ is alkenyl having 2 to 5 carbons for decreasing the viscosity and alkyl having 1 to 7 carbons for increasing the stability to ultraviolet light or for increasing the stability heat. $R^3$ is alkyl having 1 to 12 carbons, alkoxy having 1 to 12 carbons, alkoxymethyl having 2 to 12 carbons or alkenyl having 2 to 12 carbons. Desirable $R^3$ is alkenyl having 2 to 5 carbons for decreasing the viscosity, and alkyl having 1 to 7 carbons for increasing the stability to ultraviolet light or for increasing the stability to heat.

Desirable alkyl is methyl, ethyl, propyl, butyl, pentyl, hexyl, heptyl or octyl. More desirable alkyl is ethyl, propyl, butyl, pentyl or heptyl for decreasing the viscosity.

Desirable alkoxy is methoxy, ethoxy, propoxy, butoxy, pentyloxy, hexyloxy or heptyloxy. More desirable alkoxy is methoxy or ethoxy for decreasing the viscosity.

Desirable alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. More desirable alkenyl is vinyl, 1-propenyl, 3-butenyl or 3-pentenyl for decreasing the viscosity. A desirable configuration of —CH═CH— in the alkenyl depends on the position of the double bond. Trans is preferable in the alkenyl such as 1-propenyl, 1-butenyl, 1-pentenyl, 1-hexenyl, 3-pentenyl and 3-hexenyl for decreasing the viscosity and for something. C is preferable in the alkenyl such as 2-butenyl, 2-pentenyl and 2-hexenyl.

Desirable examples of alkenyl in which arbitrary hydrogen is replaced by fluorine are 2,2-difluorovinyl, 3,3-difluoro-2-propenyl, 4,4-difluoro-3-butenyl, 5,5-difluoro-4-pentenyl and 6,6-difluoro-5-hexenyl. More desirable examples are 2,2-difluorovinyl and 4,4-difluoro-3-butenyl for decreasing the viscosity.

Alkyl, alkoxy or alkenyl are straight or branched, but not cyclic. A straight-chain terminal group is preferable to a branched-chain terminal group.

The ring A, the ring B, the ring C and the ring D are each independently 1,4-cyclohexylene, 1,4-phenylene, 2-fluoro-1,4-phenylene, 3-fluoro-1,4-phenylene, 3,5-difluoro-1,4-phenylene, 2,5-difluoro-1,4-phenylene or tetrahydropyran-2,5-diyl, and arbitrary two ring D may be the same groups or different groups when m is 2. Desirable ring A, the ring B, the ring C or the ring D is 1,4-phenylene or 3-fluoro-1,4-phenylene for increasing the optical anisotropy, and 1,4-cyclohexylene for decreasing the viscosity. The ring E is 1,4-cyclohexylene, 1,4-phenylene, 2-fluoro-1,4-phenylene, 3-fluoro-1,4-phenylene, 3,5-difluoro-1,4-phenylene or tetrahydropyran-2,5-diyl. Desirable ring E is 1,4-phenylene for increasing the optical anisotropy, and 1,4-cyclohexylene for decreasing the viscosity. The ring F is 1,4-cyclohexylene, 1,4-phenylene, 2-fluoro-1,4-phenylene, 3-fluoro-1,4-phenylene, 3,5-difluoro-1,4-phenylene, 1,3-dioxane-2,5-diyl or tetrahydropyran-2,5-diyl. Desirable ring F is 1,4-phenylene or 3-fluoro-1,4-phenylene for increasing the optical anisotropy, and 1,4-cyclohexylene for increasing the maximum temperature. The ring G is 1,4-cyclohexylene, 1,4-phenylene, 2-fluoro-1,4-phenylene, 3-fluoro-1,4-phenylene, 3,5-difluoro-1,4-phenylene, 1,3-dioxane-2,5-diyl or tetrahydropyran-2,5-diyl, and arbitrary two ring G may be the same groups or different groups when n is 2 or 3. Desirable ring G is 1,4-phenylene or 3-fluoro-1,4-phenylene for increasing the optical anisotropy, 1,4-cyclohexylene for increasing the maximum temperature, and 1,3-dioxane-2,5-diyl for increasing the dielectric anisotropy. With regard to the configuration of 1,4-cyclohexylene, trans is preferable to cis for increasing the maximum temperature.

$Z^1$ and $Z^2$ are each independently a single bond, ethylene or carbonyloxy, and arbitrary two $Z^1$ may be the same groups or different groups when m is 2, and arbitrary two $Z^2$ may be the same groups or different groups when n is 2 or 3. Desirable $Z^1$ is a single bond for decreasing the viscosity, and carbonyloxy for increasing the maximum temperature. Desirable $Z^2$ is a single bond or ethylene for decreasing the viscosity, and carbonyloxy for increasing the dielectric anisotropy.

$X^1$, $X^2$, $X^3$, $X^4$, $X^5$, $X^6$ and $X^7$ are each independently hydrogen or fluorine. Desirable $X^1$, $X^2$, $X^3$, $X^4$, $X^5$, $X^6$ or $X^7$ is fluorine for increasing the dielectric anisotropy.

$Y^1$, $Y^2$, $Y^3$, $Y^4$ and $Y^5$ are each independently fluorine, chlorine or trifluoromethoxy. Desirable $Y^1$, $Y^2$, $Y^3$, $Y^4$ or $Y^5$ is fluorine for decreasing the viscosity.

m is 0, 1 or 2. Desirable m is 1 or 2 for increasing the maximum temperature, and 0 for decreasing the minimum temperature. n is 1, 2 or 3. Desirable n is 3 for increasing the maximum temperature, and 2 for decreasing the minimum temperature.

Fifth, examples of the component compounds will be shown. In the desirable compounds described below, $R^1$, $R^4$, $R^5$, $R^6$ and $R^7$ are each independently alkyl having 1 to 12 carbons or alkenyl having 2 to 12 carbons. $R^2$ is alkyl having 1 to 12 carbons, alkenyl having 2 to 12 carbons, or alkenyl having 2 to 12 carbons in which hydrogen is replaced by fluorine. $R^3$ is alkyl having 1 to 12 carbons, alkoxy having 1 to 12 carbons, alkoxymethyl having 2 to 12 carbons or alkenyl having 2 to 12 carbons.

Desirable compound (1) are the compound (1-1-1) to the compound (1-1-3), the compound (1-2-1) to the compound (1-2-3), the compound (1-3-1) to the compound (1-3-3) and the compound (1-4-1) to the compound (1-4-3). More desirable compound (1) are the compound (1-1-1), the compound (1-2-1) and the compound (1-3-1). Especially desirable compound (1) are the compound (1-1-1) and the compound (1-2-1). Desirable compound (2) are the compound (2-1) to the compound (2-15). More desirable compound (2) are the compound (2-1), the compound (2-7), the compound (2-9) and the compound (2-14). Especially desirable compound (2) is the compound (2-1). Desirable compound (3) are the compound (3-1-1) to the compound (3-1-21), the compound (3-2-1) to the compound (3-2-3) and the compound (3-3-1) to the compound (3-3-3). More desirable compound (3) are the compound (3-1-1) to the compound (3-1-3), the compound (3-2-1) and the compound (3-3-1). Especially desirable compound (3) are the compound (3-1-1) and the compound (3-2-1). Desirable compound (4) are the compound (4-1) to the compound (4-18). More desirable compound (4) are the compound (4-1) to the compound (4-11). Especially desirable compound (4) are the compound (4-1) to the compound (4-5).

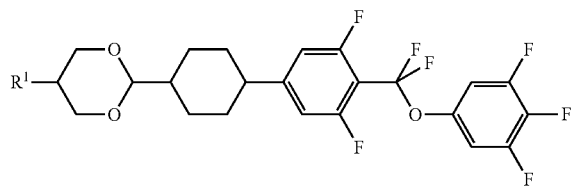

(1-1-1)

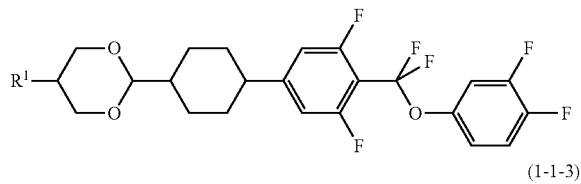

(1-1-2)

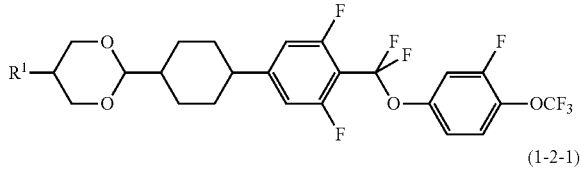

(1-1-3)

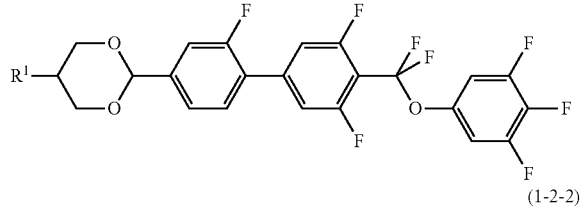

(1-2-1)

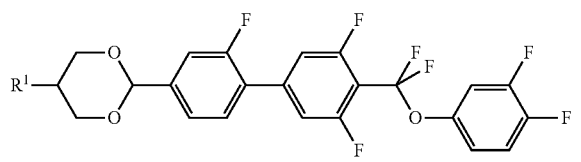

(1-2-2)

(1-2-3)
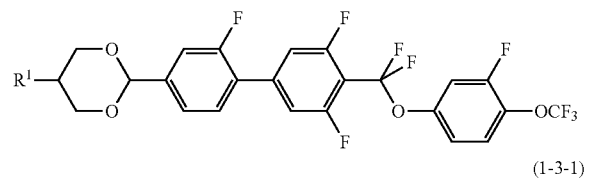
(1-3-1)
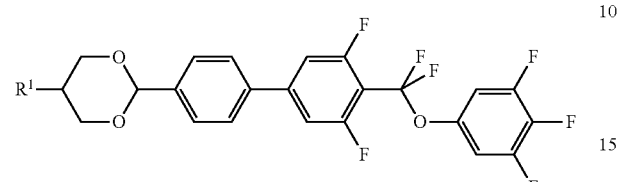
(1-3-2)
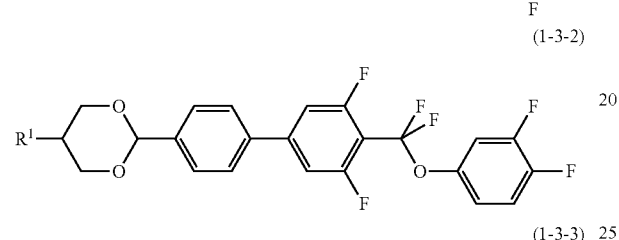
(1-3-3)
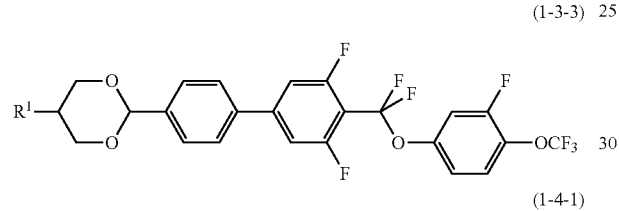
(1-4-1)
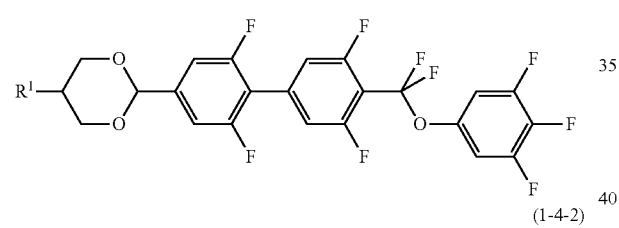
(1-4-2)
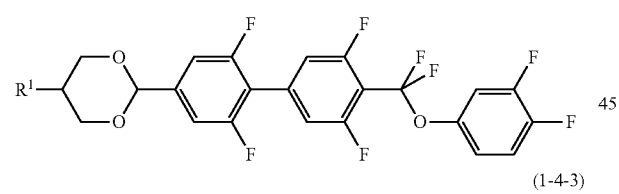
(1-4-3)
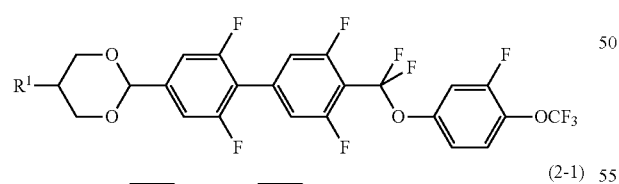
(2-1)
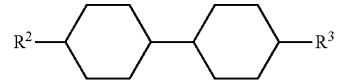
(2-2)
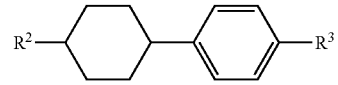
(2-3)
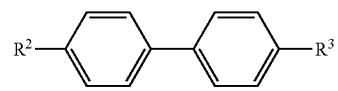
(2-4)
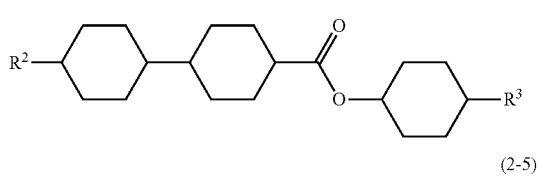
(2-5)
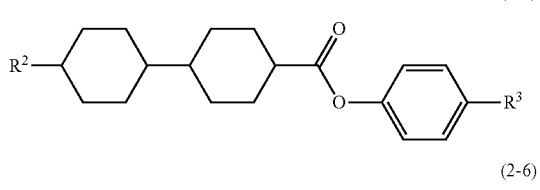
(2-6)
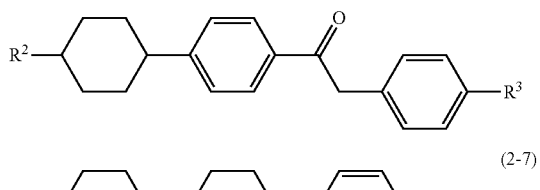
(2-7)
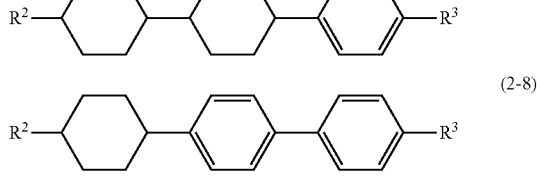
(2-8)
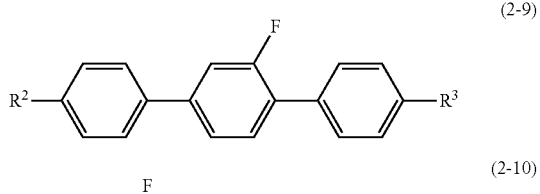
(2-9)
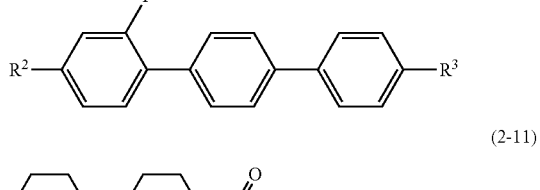
(2-10)
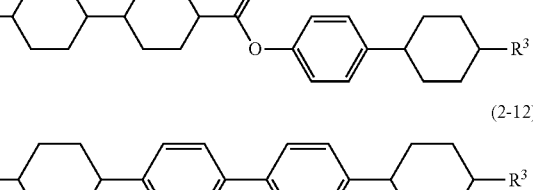
(2-11)
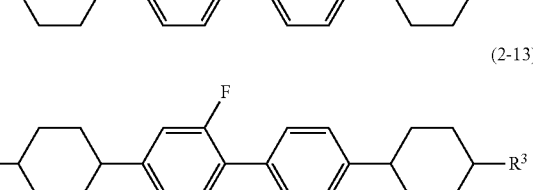
(2-12)
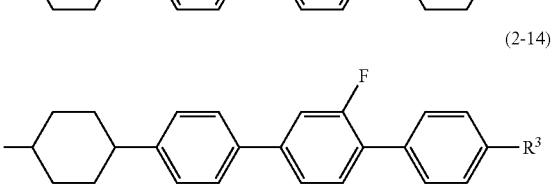
(2-13)
(2-14)

(2-15)
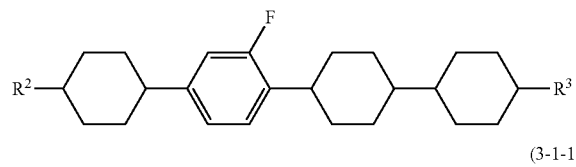
(3-1-1)
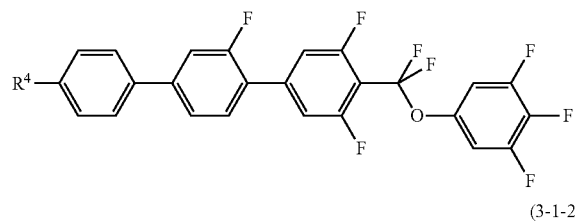
(3-1-2)
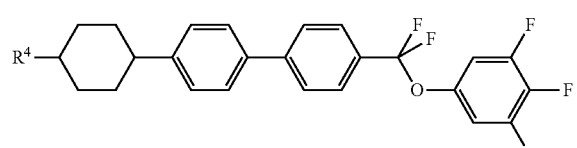
(3-1-3)
(3-1-4)
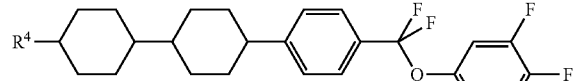
(3-1-5)
(3-1-6)
(3-1-7)
(3-1-8)
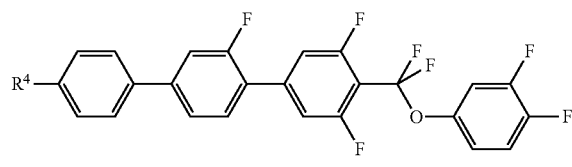
(3-1-9)
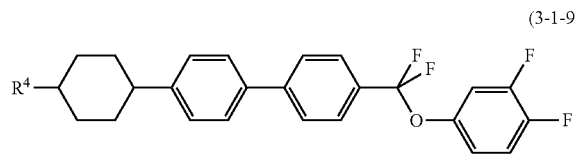
(3-1-10)
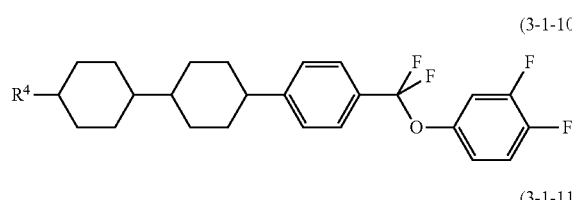
(3-1-11)
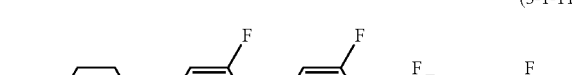
(3-1-12)
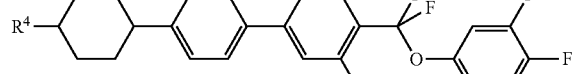
(3-1-13)
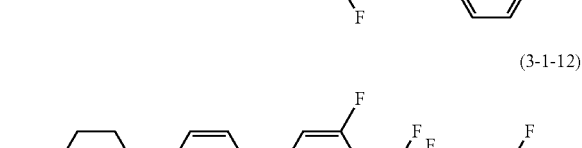
(3-1-14)
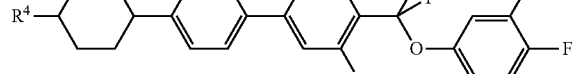
(3-1-15)
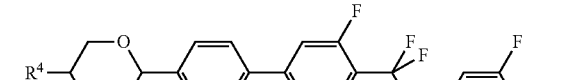
(3-1-16)
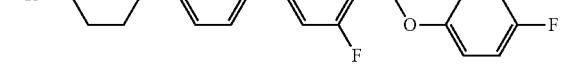

(3-1-17)
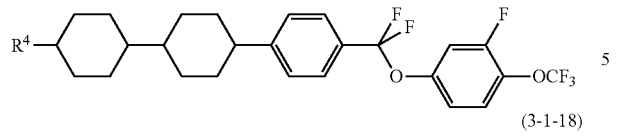
(3-1-18)
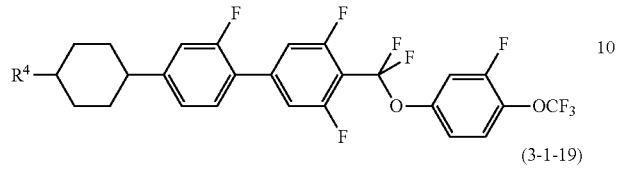
(3-1-19)
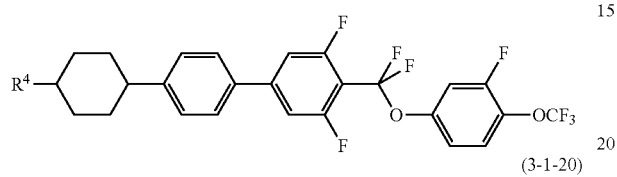
(3-1-20)
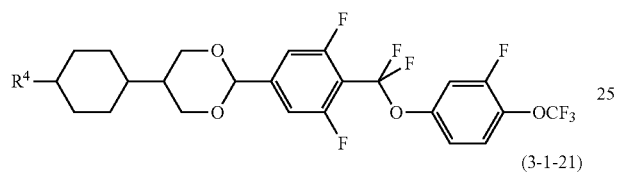
(3-1-21)
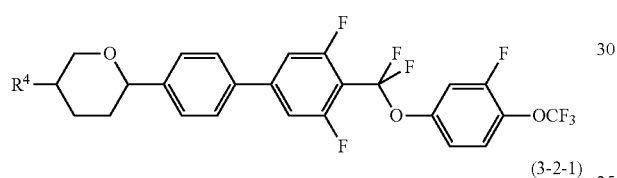
(3-2-1)
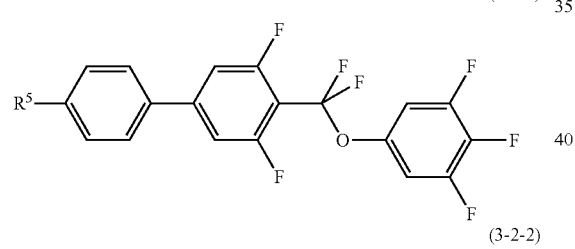
(3-2-2)
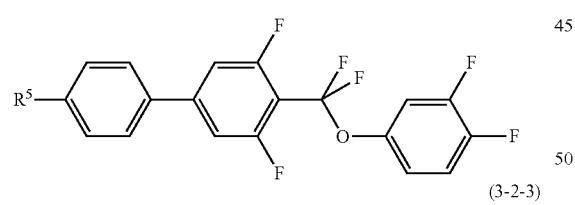
(3-2-3)
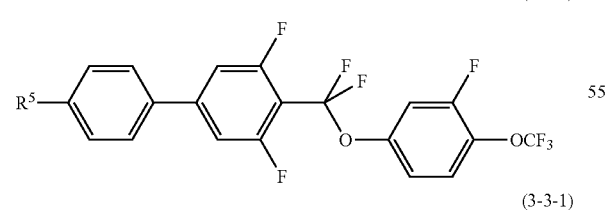
(3-3-1)
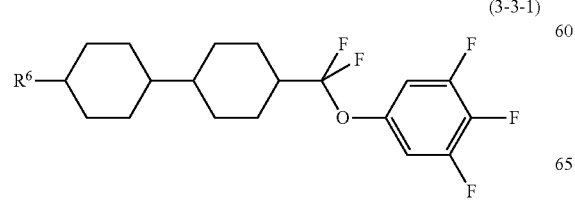
(3-3-2)
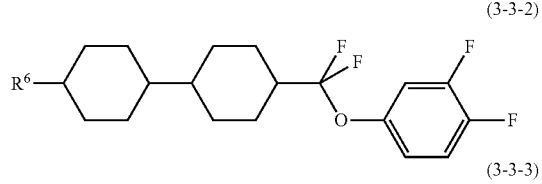
(3-3-3)
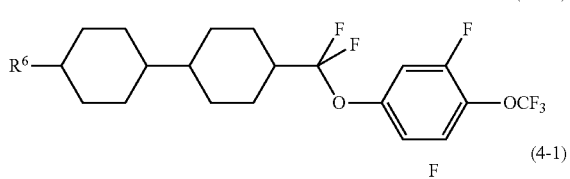
(4-1)
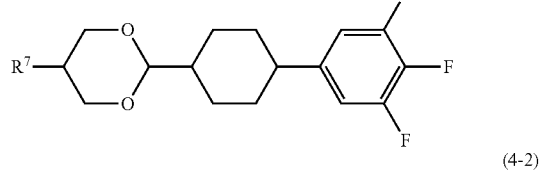
(4-2)
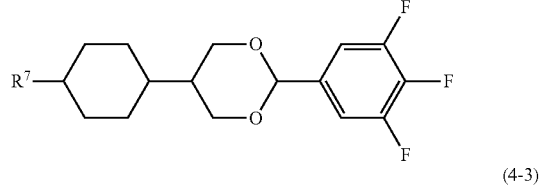
(4-3)
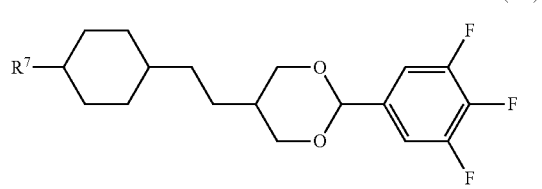
(4-4)
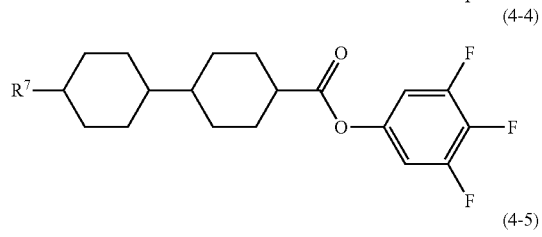
(4-5)
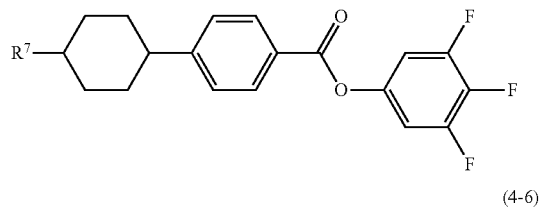
(4-6)
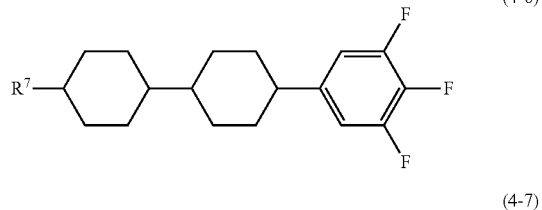
(4-7)
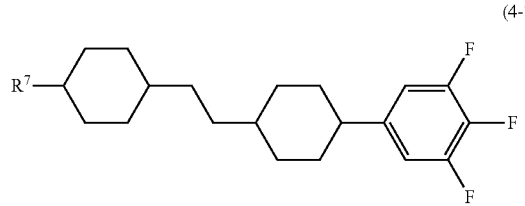

-continued

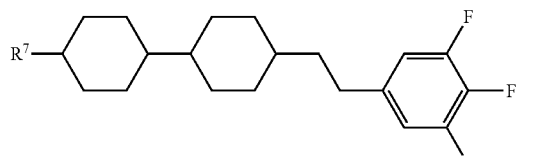
(4-8)

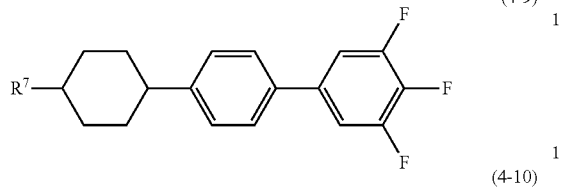
(4-9)

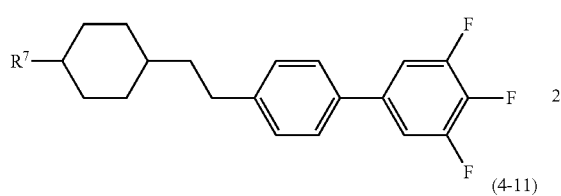
(4-10)

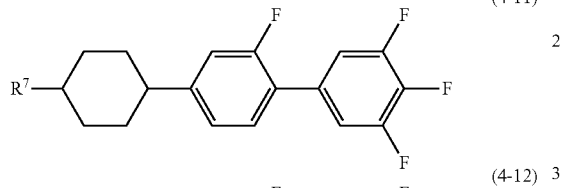
(4-11)

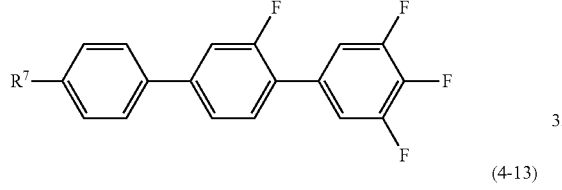
(4-12)

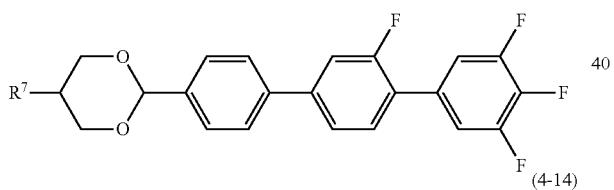
(4-13)

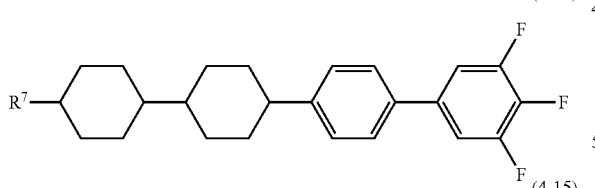
(4-14)

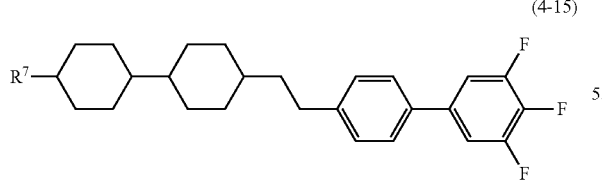
(4-15)

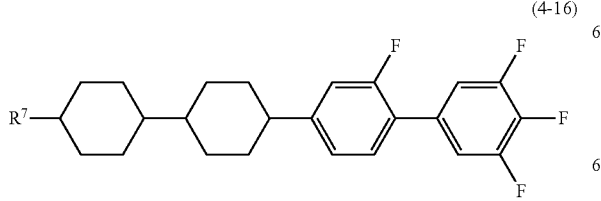
(4-16)

-continued

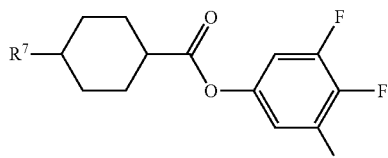
(4-17)

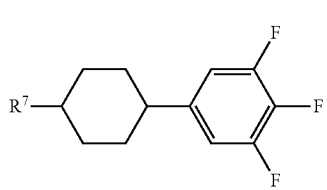
(4-18)

Sixth, additives which may be mixed with the composition will be explained. The additives include an optically active compound, an antioxidant, an ultraviolet light absorbent, a coloring matter, an antifoaming agent, a polymerizable compound and a polymerization initiator. The optically active compound is mixed with the composition for the purpose of inducing a helical structure and giving a twist angle in liquid crystals. Examples of the optically active compound include the compound (5-1) to the compound (5-5) below. A desirable ratio of the optically active compound is approximately 5% by weight or less. A more desirable ratio is in the range of approximately 0.01% to approximately 2% by weight.

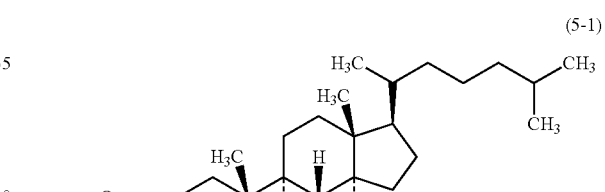
(5-1)

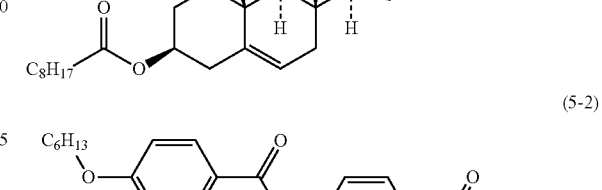
(5-2)

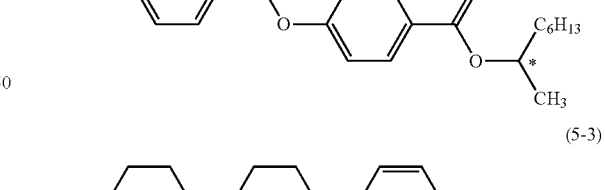
(5-3)

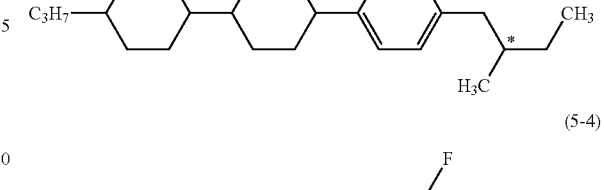
(5-4)

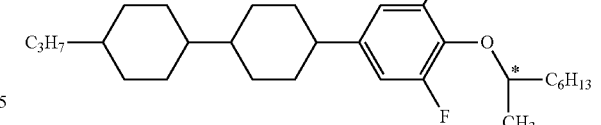

(5-5)

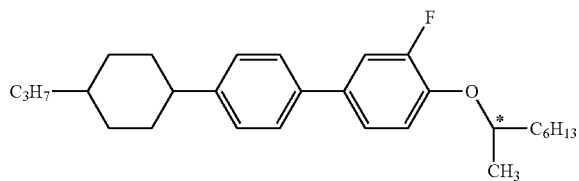

An antioxidant is mixed with the composition in order to prevent a decrease in specific resistance caused by heating under air, or to maintain a large voltage holding ratio at room temperature and also at a temperature close to the maximum temperature of a nematic phase even after the device has been used for a long time.

(6)

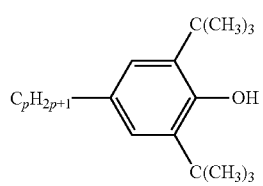

Desirable examples of the antioxidant include the compound (6) where p is an integer from 1 to 9. In the compound (6), desirable p is 1, 3, 5, 7 or 9. More desirable p is 1 or 7. The compound (6) where p is 1 is effective in preventing a decrease of the specific resistance caused by heating under air because it has a large volatility. The compound (6) where p is 7 is effective in maintaining a large voltage holding ratio at room temperature and also at a temperature close to the maximum temperature of a nematic phase even after the device has been used for a long time, because it has a small volatility. A desirable ratio of the antioxidant is approximately 50 ppm or more for achieving its effect and is approximately 600 ppm or less for avoiding a decrease of the maximum temperature or avoiding an increase of the minimum temperature. A more desirable ratio is in the range of approximately 100 ppm to approximately 300 ppm.

Desirable examples of the ultraviolet light absorbent include a benzophenone derivative, a benzoate derivative and a triazole derivative. A light stabilizer such as an amine having steric hindrance is also desirable. A desirable ratio of the ultraviolet light absorbent or the light stabilizer is approximately 50 ppm or more for achieving its effect and is approximately 10,000 ppm or less for avoiding a decrease of the maximum temperature or avoiding an increase of the minimum temperature. A more desirable ratio is in the range of approximately 100 ppm to approximately 10,000 ppm.

A dichroic dye such as an azo dye or an anthraquinone dye is mixed with the composition for adjusting to a device having a guest host (GH) mode. A desirable ratio of the coloring matter is in the range of approximately 0.01% to approximately 10% by weight. An antifoaming agent such as dimethyl silicone oil or methyl phenyl silicone oil is mixed with the composition for preventing foam formation. A desirable ratio of the antifoaming agent is approximately 1 ppm or more for achieving its effect and is approximately 1,000 ppm or less for preventing a poor display. A more desirable ratio is in the range of approximately 1 ppm to approximately 500 ppm.

A polymerizable compound is mixed with the composition for adjusting to a device having a polymer sustained alignment (PSA) mode. Desirable examples of the polymerizable compound include compounds having a polymerizable group, such as acrylates, methacrylates, vinyl compounds, vinyloxy compounds, propenyl ethers, epoxy compounds (oxiranes, oxetanes) and vinyl ketones. Especially desirable examples of the polymerizable compound are acrylate derivatives or methacrylate derivatives. A desirable ratio of the polymerizable compound is approximately 0.05% by weight or more for achieving its effect and is approximately 10% by weight or less for preventing a poor display. A more desirable ratio is in the range of approximately 0.1% to approximately 2% by weight. The polymerizable compound is preferably polymerized on irradiation with ultraviolet light or the like in the presence of a suitable initiator such as a photopolymerization initiator. Suitable conditions for polymerization, suitable types of the initiator and suitable amounts thereof are known to a person skilled in the art and are described in the literature. For example, Irgacure 651 (registered trademark), Irgacure 184 (registered trademark) or Darocure 1173 (registered trademark) (Ciba Japan K.K.), each of which is a photopolymerization initiator, is suitable for radical polymerization. A desirable ratio of the photopolymerization initiator is preferably in the range of approximately 0.1% to approximately 5% by weight and an especially desirable ratio is in the range of approximately 1% to approximately 3% by weight, based on the total weight of the polymerizable compound.

Seventh, methods for synthesizing the component compounds will be explained.

Preparation of the Compound (1)

The liquid crystal compound represented by formula (1) can be prepared by means of a combination of synthetic techniques in synthetic organic chemistry. Methods for an introduction of targeted terminal groups, rings and bonding groups to starting materials are described in books such as Organic Syntheses (John Wiley & Sons, Inc), Organic Reactions (John Wiley & Sons, Inc), Comprehensive Organic Synthesis (Pergamon Press), "Vol. 14, Synthesis and Reaction of Organic Compounds" (1978) in New Experimental Chemistry Course (Shin Jikken Kagaku Kouza, in Japanese title; Maruzen Co., Ltd.), or "Vol. 19 to Vol. 26, Organic Synthesis I to VIII" (1991) in Experimental Chemistry Course (Jikken Kagaku Kouza, in Japanese title; the fourth edition, Maruzen Co., Ltd.).

Preparation of the Compound (1-1)

One example of the preparation of the compound (1-1) is shown below as an example of the preparation of the compound (1). In the scheme, $R^1$ is alkyl having 1 to 12 carbons or alkenyl having 2 to 12 carbons; $X^1$ is hydrogen or fluorine; and $Y^1$ is fluorine, chlorine or trifluoromethoxy; those of which were already described in item 22.

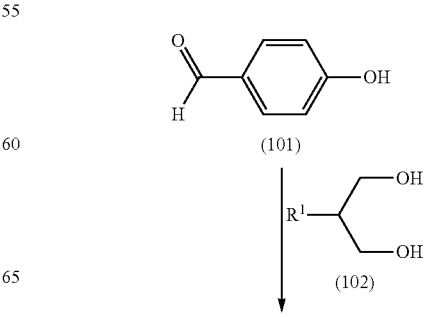

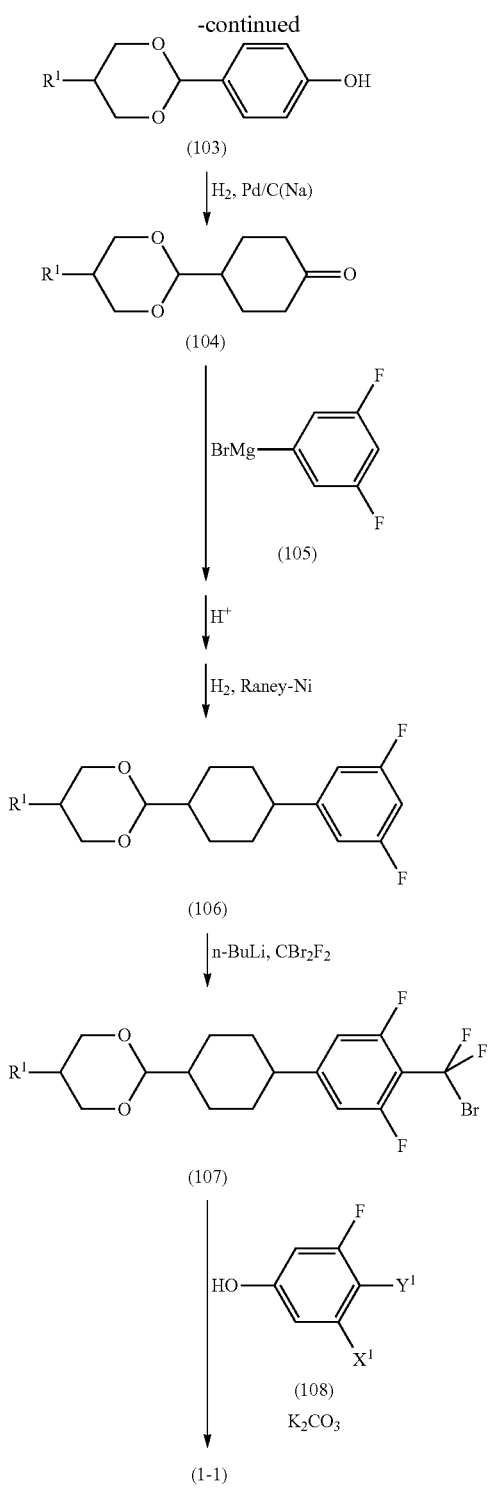

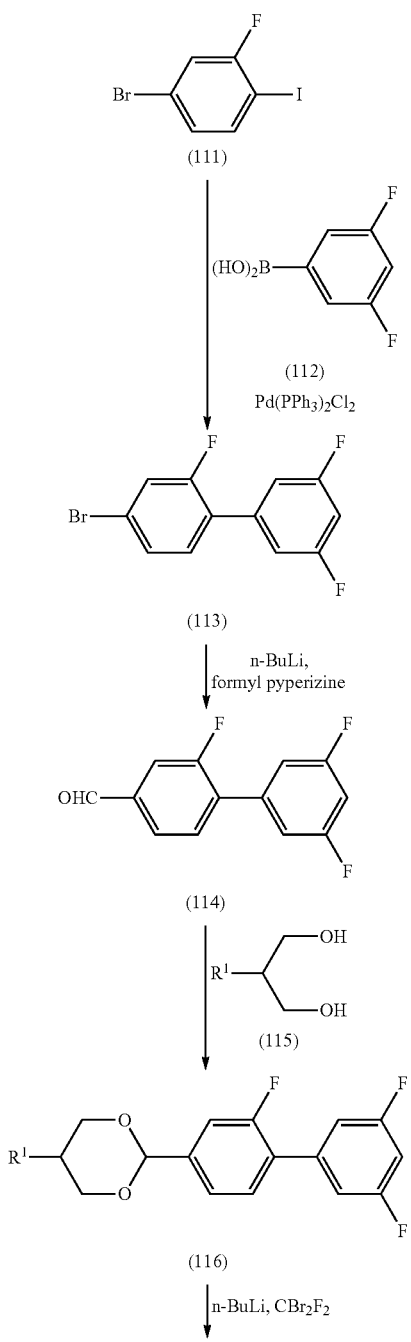

the presence of Raney nickel or a palladium catalyst to give the compound (106). The trans-isomer of the compound (106) can be isolated by means of column chromatography and recrystallization.

The compound (106) reacts with n-BuLi and then with $CF_2Br_2$ to give the compound (107). Etherification of the compound (107) with the phenol (108) in the presence of abase such as potassium carbonate gives the target compound (1-1).

Preparation of the Compound (1-2)

One example of the preparation of the compound (1-2) are as follows. In the scheme below, $R^1$ is alkyl having 1 to 12 carbons or alkenyl having 2 to 12 carbons; $X^1$ is hydrogen or fluorine; and $Y^1$ is fluorine, chlorine or trifluoromethoxy; those of which were already described in item 23.

The aldehyde (101) is commercially available as a reagent. The action of an acid such as p-toluenesulfonic acid on the mixture of the compound (101), the compound (102) and anhydrous magnesium sulfate gives the compound (103). Hydrogenation of the compound (103) in cyclohexane under pressure at 80° C. in the presence of a palladium catalyst gives the ketone (104).

The compound (104) reacts with the Grignard reagent (105) to give an alcohol derivative. The alcohol derivative is dehydrated in the presence of an acid such as p-toluenesulfonic anhydride and the resultant olefin is hydrogenated in

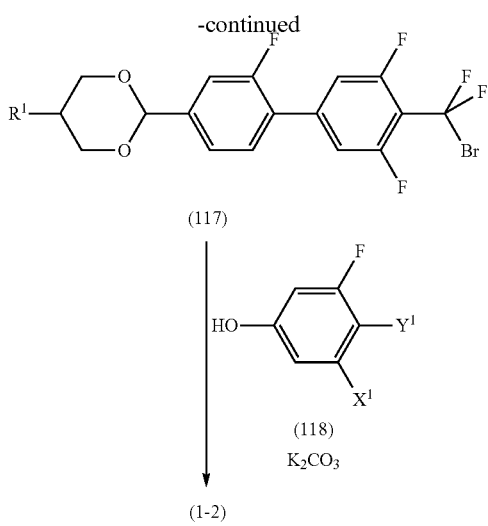

The bromobenzene (111) and the boronic acid (112) are commercially available as a reagent. The reaction of the compound (111) with the compound (112) in the presence of a palladium catalyst and a base such as potassium carbonate gives the compound (113). The compound (113) reacts with n-BuLi and then with N-formylpiperidine to give the compound (114).

Dehydrocyclization of the compound (114) with the compound (115) in the presence of an acid such as p-toluenesulfonic anhydride gives the compound (116). The compound (116) reacts with n-BuLi and then with $CF_2Br_2$ to give the compound (117). Etherification of the compound (117) with the phenol (118) in the presence of a base such as potassium carbonate gives the target compound (1-2).

Preparation of the Compounds (2) to (4)

The compounds (2) to (4) can be prepared by known methods. The synthetic methods are exemplified. The compound (2-1) is prepared by the method described in JP S59-070624 A and JP S59-176221 A. The compound (2-7) is prepared by the method described in JP S57-165328 A and JP S59-176221 A. The compound (2-9) is prepared by the method described in JP 2006-503130 A. The compound (2-14) is prepared by the method described in JP H2-237949 A. The compound (3-1) and the compound (3-2) are prepared by the method described in JP H10-251186 A. The compound (3-3) is prepared by the method described in JP H10-204016 A. The compound (4-1) is prepared by the method described in WO 98/017664 A and JP H9-012569 A. The compound (4-6) to the compound (4-10) are prepared by the method described in JP H02-233626 A. An antioxidant is commercially available. The compound of formula (6) where p is 1 is available from Sigma-Aldrich Corporation. The compound (6) where p is 7, and so forth are prepared according to the method described in U.S. Pat. No. 3,660,505.

Compounds whose synthetic methods are not described above can be prepared according to the methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Kouza, in Japanese title) (Maruzen Co., Ltd.). The composition is prepared according to known methods using the compounds thus obtained. For example, the component compounds are mixed and dissolved in each other by heating.

Last, use of the composition will be explained. The composition mainly has a minimum temperature of approximately −10° C. or lower, a maximum temperature of approximately 70° C. or higher, and an optical anisotropy in the range of approximately 0.07 to approximately 0.20. The device containing the composition has a large voltage holding ratio. The composition is suitable for an AM device. The composition is suitable especially for an AM device having a transmission type. The composition having an optical anisotropy in the range of approximately 0.08 to approximately 0.25, and further in the range of approximately 0.10 to approximately 0.30 may be prepared by adjusting ratios of the component compounds or by mixing with any other liquid crystal compound. The composition can be used as a composition having a nematic phase and as an optically active composition by adding an optically active compound.

Desirable maximum temperature is approximately 70° C. or higher. More desirable maximum temperature is approximately 80° C. or higher. Especially desirable maximum temperature is approximately 90° C. or higher.

Desirable minimum temperature is approximately 0° C. or lower. More desirable minimum temperature is approximately −20° C. or lower. Especially desirable minimum temperature is approximately −30° C. or lower.

Desirable optical anisotropy (25° C.) at 589 nm is in the range of approximately 0.07 to approximately 0.20. More desirable optical anisotropy is in the range of approximately 0.07 to approximately 0.16. Especially desirable optical anisotropy is in the range of approximately 0.08 to approximately 0.13.

Desirable dielectric anisotropy at 25° C. is approximately 5 or more, more desirable dielectric anisotropy is approximately 10 or more and especially desirable dielectric anisotropy is approximately 17 or more.

The composition can be used for an AM device. It can also be used for a PM device. The composition can also be used for the AM and PM devices having a mode such as PC, TN, STN, ECB, OCB, IPS, FFS, VA or PSA. It is especially desirable to use the composition for the AM device having the TN, OCB, IPS or FFS mode. In the AM device having the IPS mode or the FFS mode, the orientation of liquid crystal molecules may be parallel or perpendicular to a glass substrate when no voltage is applied. These devices may be of a reflection type, a transmission type or a semi-transmission type. It is desirable to use the composition for a device having the transmission type. It can be used for an amorphous silicon-TFT device or a polycrystal silicon-TFT device. The composition is also usable for a nematic curvilinear aligned phase (NCAP) device prepared by microcapsulating the composition, and for a polymer dispersed (PD) device in which a three-dimensional network-polymer is formed in the composition.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to limit the scope of the invention.

EXAMPLES

The invention will be explained in detail by way of Synthetic Examples. The invention is not limited by Synthetic Examples described below.

Synthetic Example 1

Preparation of the Compound (1-1-a)

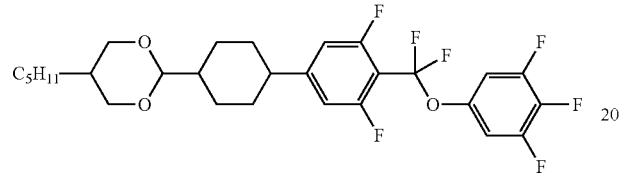

(1-1-a)

This is a compound of formula (1-1) where $R^1$ is $C_5H_{11}$, and both $X^1$ and $Y^1$ are fluorine.

The synthetic scheme is shown below.

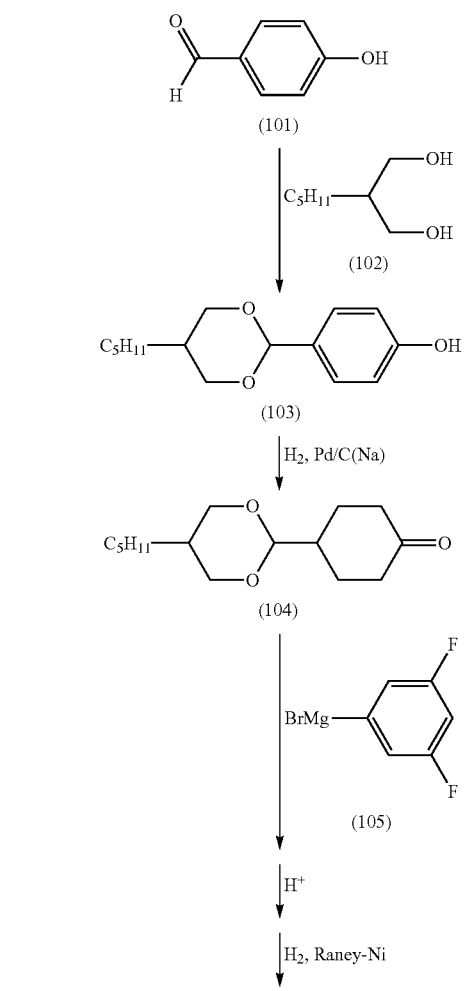

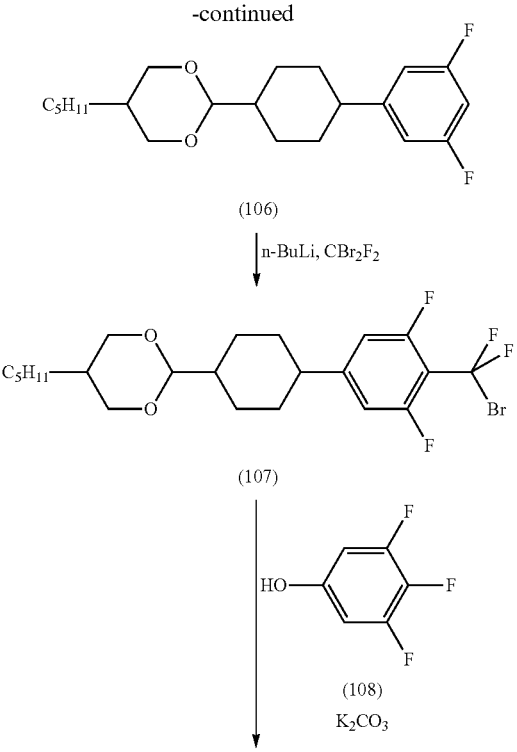

First Step

Preparation of the Compounds (103) and (104)

A mixture of 4-hydroxybenzaldehyde (101) (20.0 g, 0.164 mol), 2-pentylpropane-1,3-diol (102) (26.8 g, 0.183 mol), anhydrous magnesium sulfate (20.0 g), p-toluenesulfonic acid (0.80 g) and toluene (100 mL) was stirred at 40° C. for 3 hours. After the reaction had been completed, the reaction mixture was filtered and the filtrate was washed with water. The toluene was distilled off from the filtrate and the residue was purified by means of silica gel chromatography (eluent: toluene/ethyl acetate=5/1 by volume), giving the compound (103) (38.8 g, 0.155 mol) in 94% yield.

Pd/C (1.6 g; A-type; N.E. Chemcat Corporation) was added to a cyclohexane (150 mL) solution of the compound (103) (38.8 g, 0.155 mol), and the mixture was stirred at 70° C. for 5 hours under an atmosphere of hydrogen at 0.5 MPa. After the reaction had been completed, the palladium catalyst in the reaction mixture was filtered off. The cyclohexane was distilled off from the filtrate and the residue was purified by means of silica gel chromatography (eluent: toluene/ethyl acetate=5/1 by volume), giving the compound (104) (24.1 g, 0.0946 mol) in 61% yield.

Second Step

Preparation of the Compound (106)

A THF (80 mL) solution of 1-Bromo-3,5-difluorobenzene (105) (19.5 g, 0.101 mol) was slowly added to fine particles of magnesium (2.46 g, 0.101 mol) in THF (30 mL) under an atmosphere of nitrogen, keeping the temperature at 30 to 40° C., and the Grignard reagent was stirred at 30° C. for another 1 hour. Then, a THF solution of the compound (104) (21.4 g, 0.0842 mol) prepared in the preceding step was added to the Grignard reagent, keeping the temperature at 30 to 40° C., and the stirring was continued for another 1 hour. After the reaction had been completed, the reaction mixture was slowly poured into a 3N—HCl solution and then extracted with toluene (300 mL). The extract was washed with water three times, and the toluene was distilled off, giving the crude alcohol derivative (28.4 g, 0.0771 mol).

p-Toluenesulfonic acid (0.85 g) was added to a toluene (100 mL) solution of the alcohol (28.4 g, 0.0771 mol) and the mixture was heated under reflux at 110° C., while water being distilled was removed. After the reaction had been completed, the reaction mixture was washed with water three times. The toluene was distilled off and the residue was purified by means of silica gel chromatography (eluent: toluene), and then recrystallization (solvent: ethanol/heptane=1/1 by volume) three times, giving the trans-isomer of the cyclohexene (16.8 g, 0.0478 mol).

A Raney-Ni catalyst (1.68 g) was added to a mixture of the cylohexene (16.8 g, 0.0478 mol) obtained, toluene (30 mL) and ethanol (60 mL), and the mixture was stirred at 30° C. for 6 hours under an atmosphere of hydrogen at 0.5 MPa. After the reaction had been completed, the Ni catalyst was filtered off from the reaction mixture. The solvent was distilled off and the residue was purified by means of silica gel chromatography (eluent: toluene/n-heptane=2/1 by volume), giving the trans-isomer of the compound (106) (8.20 g, 0.0233 mol) in 28% yield.

Third Step

Preparation of the Compound (107)

n-BuLi inn-hexane solution (16 mL, 1.57 mol/L) was added to a THF (80 mL) solution of the compound (106) (8.00 g, 0.0227 mol) prepared in the preceding step at −40° C. under an atmosphere of nitrogen, and the mixture was stirred at the same temperature for another 1 hour. Then, a THF (10 mL) solution of dibromodifluoromethane (5.25 g, 0.0250 mol) was slowly added thereto, and the stirring was continued at the same temperature for 30 minutes. After the reaction had been completed, the reaction mixture was poured into water, and extracted with toluene (200 mL). The extract was washed with water three times, and the toluene was distilled off. The residue was purified by means of silica gel chromatography (eluent: toluene/heptane=1/1 by volume), giving the compound (107) (5.68 g; purity 31%; 0.00366 mol).

Fourth Step

Preparation of the Compound (1-1-a)

A mixture of 3,4,5-trifluorophenol (108) (0.596 g, 4.03 mmol), potassium carbonate (1.06 g, 7.69 mmol), tetrabutylammonium bromide (0.117 g, 0.366 mmol) and DMF (30 mL) was stirred at 40° C. for 30 minutes under an atmosphere of nitrogen. Then, a DMF (20 mL) solution of the compound (107) (5.68 g; 31% purity; 3.66 mmol) prepared in the preceding step was slowly added thereto, and the stirring was continued at 90° C. for another 1 hour. After the reaction had been completed, the reaction mixture was poured into water and extracted with toluene (200 mL). The extract was washed sequentially with an aqueous solution of sodium hydrogencarbonate once and water three times, and toluene was distilled off. The residue was purified by means of silica gel chromatography (eluent: toluene/heptane=2/1 by volume) and then recrystallization (solvent: heptane/ethanol=1/1 by volume), giving the titled compound (1-1-a) (0.221 g, 0.403 mmol) in 11% yield.

$^1$H-NMR (δ ppm, CDCl$_3$): 0.797 to 0.825 (t, 3H), 0.947 to 0.962 (m, 2H), 1.16 to 1.32 (m, 11H), 1.85 to 1.92 (m, 5H), 2.40 to 2.42 (tt, 1H), 3.20 to 3.25 (t, 2H), 4.00 to 4.15 (d, 1H) 6.75 to 6.77 (d, 2H) and 6.87 to 6.90 (dd, 2H).

$^{19}$F-NMR (δ ppm, CDCl$_3$): −62.1 to −62.2 (t, 2F), −111.9 to −112.0 (dt, 2F), 133.0 to −133.1 (dd, 2F) and −163.7 to −163.8 (tt, 1F).

Phase transition temperature of the resultant compound (1-1-a) was as follows. A differential scanning calorimeter Model Diamond-DSC (PerkinElmer Inc.) was used for measurement.

Phase transition temperature: C, 70.9; C, 74.8; N, 121.9; Iso.

A composition was prepared by mixing 10% by weight of the compound (1-1-a) prepared in Synthetic Example 1 with 90% by weight of the mother liquid crystals that will be described later, and characteristics were calculated from the mixing ratio and the measured values by means of extrapolation.

NI=88.7° C., Δn=0.097, Δ∈=33.4.

Synthetic Example 2

Preparation of the Compound (1-2-a)

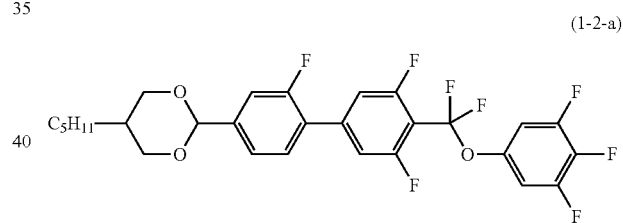

This is a compound of formula (1-2) where $R^1$ is $C_5H_{11}$, and both $X^1$ and $Y^1$ are fluorine.

The synthetic scheme is shown below.

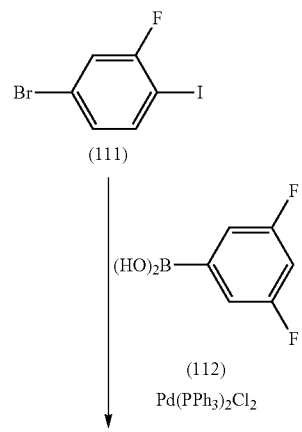

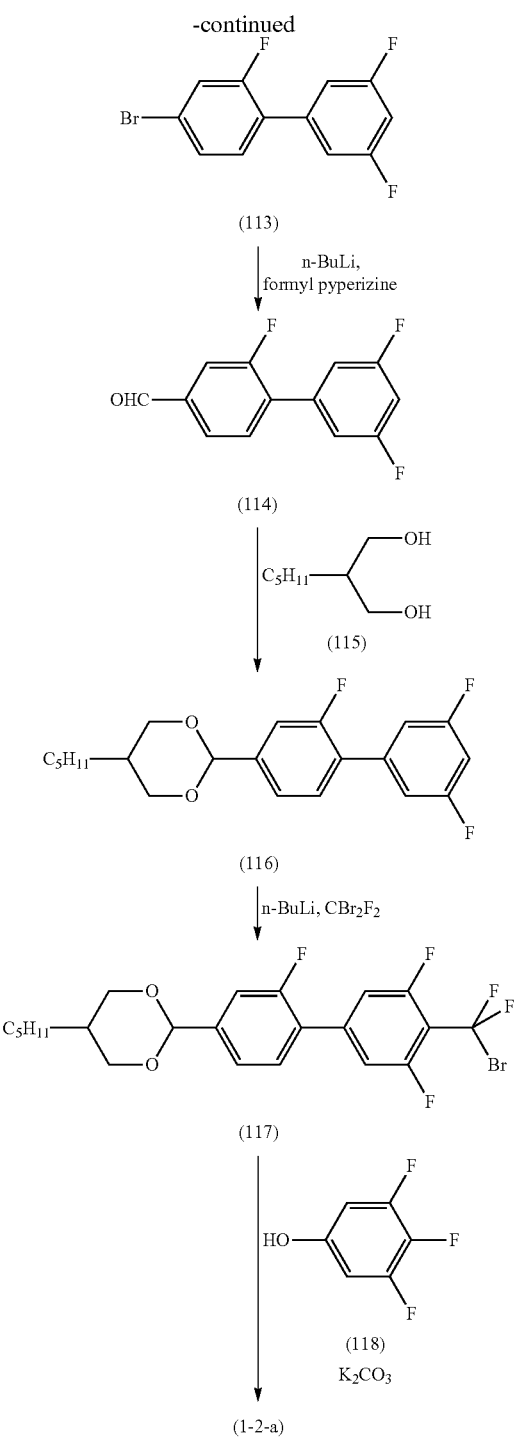

First Step

Preparation of the Compound (113)

Pd(PPh$_3$)$_2$Cl$_2$ (1.16 g, 0.00166 mol) was added to a mixture of the bromobenzene (111) (50.0 g, 0.166 mol), the boronic acid (112) (28.7 g, 0.183 mol), potassium carbonate (34.4 g, 0.249 mol), triphenylphosphine (0.871 g, 0.00332 mol), toluene (100 mL), ethanol (100 mL) and water (10 mL), and the stirring was continued at 80° C. for another 8 hours. After the reaction had been completed, the reaction mixture was poured into water, and extracted with toluene (100 mL). The extract was washed sequentially with an aqueous solution of sodium hydrogencarbonate once and water three times, and the toluene was distilled off. The residue was purified by means of silica gel chromatography (eluent: heptane) and then recrystallization (solvent: heptane/ethanol=1/1 by volume), giving the compound (113) (32.4 g, 0.113 mol) in 68% yield.

Second Step

Preparation of the Compound (114)

A Grignard reaction was initiated by the addition of a small amount of a THF (50 mL) solution of the compound (113) (25.5 g, 0.526 mol) prepared in the preceding step, to magnesium (2.59 g, 0.107 mol) in THF (5 mL) and then by heating, under an atmosphere of nitrogen. The rest of the THF solution of the compound (113) slowly was added thereto while the reaction temperature was keeping at 20 to 30° C., and the stirring was continued at the same temperature for 1 hour. Then, the Grignard reagent was cooled to 0° C., and a THF (30 mL) solution of formylpyridine (0.133 mol) was slowly added thereto, and the stirring was continued at the same temperature for another 1 hour. After the reaction had been completed, the reaction mixture was poured into 1N—HCl aqueous solution, and extracted with toluene (200 mL). The extract was washed sequentially with an aqueous solution of sodium hydrogencarbonate once and water three times, and the toluene was distilled off. The residue was purified by means of silica gel chromatography (eluent: toluene), giving the compound (114) (11.2 g, 47.4 mmol) in 42% yield.

Third Step

Preparation of the Compound (116)

p-Toluenesulfonic acid hydrate (0.30 g) was added to a toluene (80 mL) solution of the compound (114) (11.2 g, 47.5 mmol) prepared in the preceding step and the compound (115) (8.32 g, 56.9 mmol). The mixture was heated with stirring at 110° C. for 2 hours, while water being formed in a dean-stark-trap was removed. After the reaction had been completed, the reaction mixture was poured into 1N—HCl aqueous solution, and extracted with toluene (100 mL). The extract was washed sequentially with an aqueous solution of sodium hydrogencarbonate once and water three times, and the toluene was distilled off. The residue was purified by means of silica gel chromatography (eluent: toluene) and then recrystallization (solvent: ethanol/heptane=1/1 by volume), giving the compound (116) (10.0 g, 27.5 mmol) in 58% yield.

Fourth Step

Preparation of the Compound (117)

n-BuLi inn-hexane solution (21 mL, 1.57 mol/L) was added to a THF (80 mL) solution of the compound (116) (10.0 g, 27.5 mmol) prepared in the preceding step at −40° C. in an atmosphere of nitrogen, and the stirring was continued at the same temperature for 1 hour. Then, a THF (14 mL) solution of dibromodifluoromethane (6.91 g, 32.9 mmol) was slowly added thereto, and the stirring was continued at the same temperature for 30 minutes. After the reaction had been completed, the reaction mixture was poured into water, and extracted with toluene (200 mL). The extract was washed with water three times, and the toluene was distilled off. The residue was purified by means of silica gel chromatography (eluent: toluene), giving the compound (117) (13.3 g; 48% purity; 12.9 mmol).

Fifth Step

Preparation of the Compound (1-2-a)

A mixture of 3,4,5-trifluorophenol (118) (2.11 g, 14.2 mmol), potassium carbonate (3.58 g, 25.9 mmol), tetrabutylammonium bromide (0.417 g, 1.29 mmol) and DMF (30 mL) was heated with stirring at 40° C. for 30 minutes under a stream of nitrogen. Then, a DMF (50 mL) solution of the compound (117) (13.3 g; 48% purity; 12.9 mmol) prepared in the preceding step was slowly added thereto, and the stirring was continued at 90° C. for 1 hour. After the reaction had been completed, the reaction mixture was poured into water, and extracted with toluene (200 mL). The extract was washed sequentially with an aqueous solution of sodium hydrogencarbonate twice and water three times, and the toluene was distilled off. The residue was purified by means of silica gel chromatography (eluent: toluene) and then recrystallization (solvent: ethanol/ethyl acetate=1/1 by volume), giving the titled compound (1-2-a) (4.77 g, 8.51 mmol) in 66% yield.

$^1$H-NMR (δ ppm, CDCl$_3$): 0.900 to 0.914 (t, 3H), 1.09 to 1.13 (m, 2H), 1.28 to 1.34 (m, 6H), 2.11 to 2.16 (m, 1H), 3.53 to 3.57 (t, 2H), 4.24 to 4.27 (dd, 2H), 5.44 (s, 1H), 6.98 to 7.00 (dd, 2H), 7.19 to 7.21 (d, 2H) and 7.35 to 7.42 (m, 3H).

$^{19}$F-NMR (δ ppm, CDCl$_3$): −62.3 to −62.4 (t, 2F), −111.1 to −111.2 (dt, 2F), 132.9 to −133.0 (dd, 2F) and −136.7 to −163.7 (tt, 1F).

Phase transition temperature of the compound (1-2-a) obtained was as follows. A differential scanning calorimeter Model Diamond-DSC (PerkinElmer Inc.) was used for measurement.

Phase transition temperature: C, 62.4; N, 108.5; Iso.

A composition was prepared by mixing 15% by weight of the compound (1-2-a) prepared in Synthetic Example 2 with 85% by weight of the mother liquid crystals that will be described later, and characteristics were calculated from the mixing ratio and the measured values by means of extrapolation.

NI=96.4° C., Δn=0.137, Δ∈=39.1.

Synthetic Example 3

The compound (1-2) where R$^1$ is C$_3$H$_7$, and both X$^1$ and Y$^1$ are fluorine, and the compound (1-2) where R$^1$ is C$_4$H$_9$, and both X$^1$ and Y$^1$ are fluorine were prepared in addition to the compound (1-2) where R$^1$ is C$_5$H$_{11}$, and both X$^1$ and Y$^1$ are fluorine, and their characteristics were measured in the same manner. Characteristics of three compounds are shown below.

C 88.3 N 112.2 Iso
Δn: 0.144, Δε: 42.5

C 65.5 N 105.1 Iso
Δn: 0.137, Δε: 39.7

C 62.4 N 108.5 Iso
Δn: 0.137, Δε: 39.1

Methods for measurement of the components of mother liquid crystals, phase transition temperature (NI) of a nematic phase-isotropic liquid, optical anisotropy (Δn), dielectric anisotropy (Δ∈) will be described below.

A composition and a compound were a subject for measurement in order to evaluate characteristics of the composition and the compound to be included in the composition. When the subject for measurement was a composition, the composition itself was measured as a sample, and the value obtained was described here. When the subject for measurement was a compound, a sample for measurement was prepared by mixing the compound (15% by weight) with mother liquid crystals (85% by weight). Characteristic values of the compound were calculated from values obtained by measurement, according to a method of extrapolation. That is: (extrapolated value)=[(measured value of a sample)−0.85× (measured value of mother liquid crystals)]/0.15. When a smectic phase (or crystals) separated out at this ratio at 25° C., the ratio of the compound to the mother liquid crystals was changed step by step in the order of (10% by weight/90% by weight), (5% by weight/95% by weight) and (1% by weight/ 99% by weight). Values of the maximum temperature, the optical anisotropy, the viscosity and the dielectric anisotropy with regard to the compound were obtained by this extrapolation.

The components of the mother liquid crystals were as follows. The ratios were expressed as a percentage by weight.

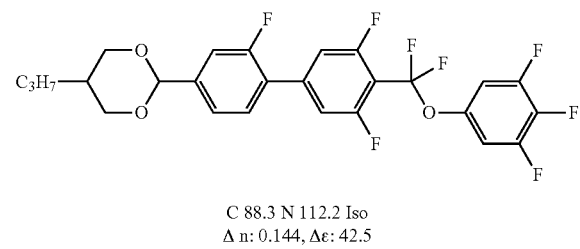

Characteristics were measured according to the following methods. Most methods are described in the Standards of Electronic Industries Association of Japan, EIAJ•ED-2521 A or those with some modifications.

Maximum Temperature of a Nematic Phase (NI; ° C.): A sample was placed on a hot plate in a melting point apparatus equipped with a polarizing microscope and was heated at the rate of 1° C. per minute. Temperature was measured when part of the sample began to change from a nematic phase to an isotropic liquid. A higher limit of the temperature range of a nematic phase may occasionally be abbreviated to "the maximum temperature."

Minimum Temperature of a Nematic Phase (Tc; ° C.): A sample having a nematic phase was put in glass vials and then kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., Tc was expressed as ≦−20° C. A lower limit of the temperature range of a nematic phase may occasionally be abbreviated to "the minimum temperature."

Viscosity (bulk viscosity; η; measured at 20° C.; mPa·s): Viscosity was measured by use of an E-type viscometer.

Viscosity (rotational viscosity; γ1; measured at 25° C.; mPa·s): Measurement was carried out according to the method described in M. Imai, et al., Molecular Crystals and Liquid Crystals, Vol. 259, 37 (1995). A sample was poured into a TN device in which the twist angle was 0 degrees and the distance between two glass substrates (cell gap) was 5 micrometers. A voltage with an increment of 0.5 volt in the range of 16 to 19.5 volts was applied stepwise to the TN device. After a period of 0.2 second with no voltage, a voltage was applied repeatedly under the conditions of only one rectangular wave (rectangular pulse; 0.2 second) and of no voltage (2 seconds). The peak current and the peak time of the transient current generated by the applied voltage were measured. The value of rotational viscosity was obtained from the measured values and the calculating equation (8) on page 40 of the paper presented by M. Imai, et al. The value of dielectric anisotropy necessary for this calculation was obtained by use of the device that had been used for the measurement of rotational viscosity, according to the method that will be described below.

Optical Anisotropy (refractive index anisotropy; Δn; measured at 25° C.): Measurement was carried out by use of an Abbe refractometer with a polarizing plate mounted on the ocular, on irradiation with light at a wavelength of 589 nanometers. The surface of the main prism was rubbed in one direction, and then a sample was dropped on the main prism. A refractive index (n∥) was measured when the direction of polarized light was parallel to that of the rubbing. A refractive index (n⊥) was measured when the direction of polarized light was perpendicular to that of the rubbing. The value of optical anisotropy was calculated from the equation: Δn∥−n⊥.

Dielectric Anisotropy (Δ∈; measured at 25° C.): A sample was poured into a TN device in which the distance between two glass substrates (cell gap) was 9 micrometers and the twist angle was 80 degrees. Sine waves (10 V, 1 kHz) were applied to this device, and a dielectric constant (∈∥) in a major axis direction of liquid crystal molecules was measured after 2 seconds. Sine waves (0.5 V, 1 kHz) were applied to the device and a dielectric constant (∈⊥) in a minor axis direction of the liquid crystal molecules was measured after 2 seconds. The value of dielectric anisotropy was calculated from the equation: Δ∈=∈∥−∈⊥.

Threshold Voltage (Vth; measured at 25° C.; V): Measurement was carried out with an LCD evaluation system Model LCD-5100 made by Otsuka Electronics Co., Ltd. The light source was a halogen lamp. A sample was poured into a TN device having a normally white mode, in which the distance between two glass substrates (cell gap) was about 0.45/Δn (micrometers) and the twist angle was 80 degrees. Voltage to be applied to the device (32 Hz, rectangular waves) was stepwise increased in 0.02 V increments from 0 V up to 10 V. During the increase, the device was irradiated with light in the perpendicular direction, and the amount of light passing through the device was measured. A voltage-transmittance curve was prepared, in which the maximum amount of light corresponded to 100% transmittance and the minimum amount of light corresponded to 0% transmittance. The threshold voltage was voltage at 90% transmittance.

Voltage Holding Ratio (VHR-1; measured at 25° C.; %): A TN device used for measurement had a polyimide-alignment film, and the distance between two glass substrates (cell gap) was 5 micrometers. A sample was poured into the device, and then the device was sealed with an adhesive curable on irradiation with ultraviolet light. A pulse voltage (60 microseconds at 5 V) was applied to the device and the device was charged. A decreasing voltage was measured for 16.7 milliseconds with a high-speed voltmeter, and the area A between a voltage curve and a horizontal axis in a unit cycle was obtained. The area B was an area without the decrease. The voltage holding ratio was a percentage of the area A to the area B.

Voltage Holding Ratio (VHR-2; measured at 80° C.; %): A TN device used for measurement had a polyimide-alignment film, and the distance between two glass substrates (cell gap) was 5 micrometer. A sample was poured into the device, and then the device was sealed with an adhesive curable on irradiation with ultraviolet light. A pulse voltage (60 microseconds at 5 V) was applied to the TN device and the device was charged. A decreasing voltage was measured for 16.7 milliseconds with a high-speed voltmeter and the area A between a voltage curve and a horizontal axis in a unit cycle was obtained. The area B was an area without the decrease. The voltage holding ratio was a percentage of the area A to the area B.

Voltage Holding Ratio (VHR-3; measured at 25° C.; %): The stability to ultraviolet light was evaluated by measuring a voltage holding ratio after irradiation with ultraviolet light. A TN device used for measurement had a polyimide-alignment film and the cell gap was 5 micrometers. A sample was poured into the device, and then the device was irradiated with light for 20 minutes. The light source was an ultra high-pressure mercury lamp USH-500D (produced by Ushio, Inc.), and the distance between the device and the light source was 20 centimeters. In this measurement of VHR-3, a decreasing voltage was measured for 16.7 milliseconds. A composition having a large VHR-3 has a high stability to ultraviolet light. The value of VHR-3 is preferably 90% or more, and more preferably 95% or more.

Voltage Holding Ratio (VHR-4; measured at 25° C.; %): A TN device into which a sample was poured was heated in a constant-temperature bath at 80° C. for 500 hours, and then the stability to heat was evaluated by measuring the voltage holding ratio. In this measurement of VHR-4, a decreasing voltage was measured for 16.7 milliseconds. A composition having a large VHR-4 has a high stability to heat.

Response Time (τ; measured at 25° C.; millisecond): Measurement was carried out with an LCD evaluation system Model LCD-5100 made by Otsuka Electronics Co., Ltd. The light source was a halogen lamp. The low-pass filter was set at 5 kHz. A sample was poured into a TN device having a normally white mode, in which the cell gap between two glass substrates was 5.0 micrometers and the twist angle was 80 degrees. Rectangular waves (60 Hz, 5 V, 0.5 second) were applied to the device. The device was simultaneously irradiated with light in the perpendicular direction, and the amount of light passing through the device was measured. The maximum amount of light corresponded to 100% transmittance, and the minimum amount of light corresponded to 0% transmittance. Rise time ($\tau r$; millisecond) was the time required for a change from 90% to 10% transmittance. Fall time ($\tau f$; millisecond) was the time required for a change from 10% to 90% transmittance. The response time was the sum of the rise time and the fall time thus obtained.

Elastic Constant (K; measured at 25° C.; pN): A LCR meter Model HP 4284-A made by Yokokawa Hewlett-Packard, Ltd was used for measurement. A sample was poured into a homogeneous alignment cell in which the distance between two glass substrates (cell gap) was 20 micrometers. An electric charge of 0 volts to 20 volts was applied to the cell, and electrostatic capacity and the applied voltage were measured. The measured values of the electrostatic capacity (C) and the applied voltage (V) were fitted to formula (2.98) and formula (2.101) in page 75 of the "Liquid Crystal Device Handbook" (The Nikkan Kogyo Shimbun, Ltd.) and the values of K11 and K33 were obtained from formula (2.99). Next, the value of K22 was calculated from formula (3.18) in page 171 using the values of K11 and K33 thus obtained. The Elastic constant was an average value of K11, K22 and K33.

Specific resistance ($\rho$; measured at 25° C.; SI cm): A sample (1.0 milliliter) was poured into a vessel equipped with electrodes. DC voltage (10V) was applied to the vessel, and the DC current was measured after 10 seconds. The specific resistance was calculated according to the following equation: (specific resistance)=[(voltage)×(electric capacity of vessel)]/[(DC current)×(dielectric constant in vacuum)].

Gas chromatographic analysis: A gas chromatograph Model GC-14B made by Shimadzu Corporation was used for measurement. The carrier gas was helium (2 milliliters per minute). The sample injector and the detector (FID) were set to 280° C. and 300° C., respectively. A capillary column DB-1 (length 30 meters, bore 0.32 millimeter, film thickness 0.25 micrometer; dimethylpolysiloxane as the stationary phase; non-polar) made by Agilent Technologies, Inc. was used for the separation of component compounds. After the column had been kept at 200° C. for 2 minutes, it was further heated to 280° C. at the rate of 5° C. per minute. A sample was dissolved in acetone (0.1% by weight), and 1 microliter of the solution was injected into the sample injector. A recorder used was a Model C-R5A Chromatopac Integrator made by Shimadzu Corporation or its equivalent. A gas chromatogram obtained showed the retention time of peaks and the peak areas corresponding to the component compounds.

Solvents for diluting the sample may also be chloroform, hexane and so forth. The following capillary columns may also be used in order to separate the component compounds: HP-1 made by Agilent Technologies Inc. (length 30 meters, bore 0.32 millimeter, film thickness 0.25 micrometer), Rtx-1 made by Restek Corporation (length 30 meters, bore 0.32 millimeter, film thickness 0.25 micrometer), and BP-1 made by SGE International Pty. Ltd. (length 30 meters, bore 0.32 millimeter, film thickness 0.25 micrometer). A capillary column CBP1-M50-025 (length 50 meters, bore 0.25 millimeter, film thickness 0.25 micrometer) made by Shimadzu Corporation may also be used for the purpose of avoiding an overlap of peaks of the compounds.

The ratio of the liquid crystal compounds included in the composition may be calculated according to the following method. The liquid crystal compounds are detected by use of a gas chromatograph. The ratio of peak areas in the gas chromatogram corresponds to the ratio (molar ratio) of the liquid crystal compounds. When the capillary columns described above are used, the correction coefficient of respective liquid crystal compounds may be regarded as one. Accordingly, the ratio (weight ratio) of the liquid crystal compounds can be calculated from the ratio of peak areas.

$^1$H-NMR Analysis: Bruker DRX 500 (produced by Bruker BioSpin Co., Ltd.) was used for measurement. A sample synthesized in the examples and so forth was dissolved in a deuterated solvent such as $CDCl_3$, in which the sample is soluble, and the measurement was carried out at room temperature and at 500 MHz with integration of 24. In the explanation of nuclear magnetic resonance spectra obtained, the terms s, d, t, q and m stand for a singlet, a doublet, a triplet, a quartet and a multiplet, respectively. Tetramethylsilane (TMS) was used as a standard substance for the zero point of chemical shifts $\delta$.

$^{19}$F-NMR Analysis: Bruker DRX 500 (produced by Bruker BioSpin Co., Ltd.) was used for measurement. A sample synthesized in the examples and so forth was dissolved in a deuterated solvent such as $CDCl_3$, in which the sample is soluble, and the measurement was carried out at room temperature and at 500 MHz with integration of 24. In the explanation of nuclear magnetic resonance spectra obtained, the terms s, d, t, q and m stand for a singlet, a doublet, a triplet, a quartet and a multiplet, respectively. Trichlorofluoromethane was used as a standard substance for the zero point of chemical shifts $\delta$.

Phase Structure and Transition Temperature (° C.): Measurements were carried out according to the following methods (1) and (2).

(1) A compound was placed on a hot plate of a melting point apparatus (Hot Stage Model FP-52 made by Mettler Toledo International Inc.) equipped with a polarizing microscope, and the phase conditions and their changes were observed with the polarizing microscope, specifying the kinds of a liquid crystal phase while the compound was heated at the rate of 3° C. per minute.

(2) A sample was heated and then cooled at a rate of 3° C. per minute using a Perkin-Elmer differential scanning calorimeter, a DSC-7 System or a Diamond DSC System. The starting point of an endothermic peak or an exothermic peak caused by a phase change of the sample was obtained by means of the extrapolation and the phase transition temperature was determined.

The symbol C stood for crystals, which were expressed as $C_1$ or $C_2$ when the kinds of the crystals were distinguishable. The symbols Sm and N stood for a smectic phase and a nematic phase, respectively. The symbol I stood for a liquid (isotropic). The symbols SmA and SmB stood for a smectic A phase and a smectic B phase, respectively, when they were distinguishable. The symbol BP stands for a blue phase or an optically isotropic liquid crystal phase. Two-phase existence is expressed in the form such as (N*+I) or (N*+BP). Specifically, (N*+I) expresses a coexistent phase of a chiral nematic phase and a non-liquid crystal isotropic phase, and (N*+BP) expresses a coexistent phase of a chiral nematic phase, and a blue phase or an optically isotropic liquid crystal phase. The symbol Un stands for an unidentified phase that is not optically isotropic. Phase-transition temperatures were expressed as, for example, "C 50.0 N 100.0 I", which means that the phase-transition temperature (CN) from crystals to a nematic phase is 50.0° C., and the phase-transition temperature (NI) from the nematic phase to a liquid is 100.0° C. The same applied to the other transition temperatures.

The invention will be explained in detail by way of Examples. The invention is not limited by Examples described below. The compounds described in Comparative Examples and Examples were expressed as symbols according to the definition in the following Table 3. In Table 3, the configuration of 1,4-cyclohexylene is trans. A parenthesized number next to the symbolized compound in Example corresponds to a compound number. The symbol (–) means any other liquid crystal compound. Ratios (percentage) of liquid crystal compounds mean the percentages by weight (% by weight) based on the total weight of the liquid crystal composition. The liquid crystal composition further includes an impurity. Last, characteristics of the composition are summarized.

TABLE 3

| Method of Description of Compounds using Symbols R—(A$_1$)—Z$_1$—...—Z$_n$—(A$_n$)—R' | |
|---|---|
| 1) Left-Teminal Group R— | Symbol |
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—(CH$_2$)$_2$— | VFF2— |
| 2) Right-Terminal Group —R' | Symbol |
| —C$_n$H$_{2n+1}$ | -n |
| —OC$_n$H$_{2n+1}$ | —On |
| —F | —F |
| —Cl | —CL |
| —OCF$_3$ | —OCF3 |
| —CH=CH$_2$ | —V |
| —CH=CH—C$_n$H$_{2n+1}$ | —Vn |
| —C$_n$H$_{2n}$—CH=CH$_2$ | —nV |
| —CH=CF$_2$ | —VFF |
| 3) Bonding Group —Z$_n$— | Symbol |
| —C$_2$H$_4$— | 2 |
| —COO— | E |
| —CH=CH— | V |
| —C≡C— | T |
| —CF$_2$O— | X |
| 4) Ring Structure —A$_n$— | Symbol |
|  | H |
|  | B |
| 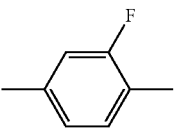 | B(F) |
| 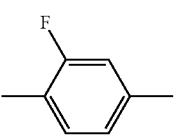 | B(2F) |

TABLE 3-continued

| Method of Description of Compounds using Symbols R—(A$_1$)—Z$_1$—...—Z$_n$—(A$_n$)—R' | |
|---|---|
| 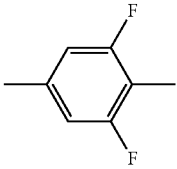 | B(F,F) |
| 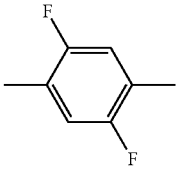 | B(2F,5F) |
| 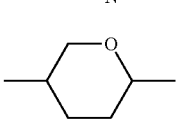 | Py |
| 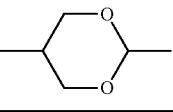 | dh |
| 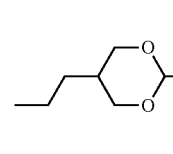 | G |
| 5) Examples of Description | |

Example 1. 3-GB(F)B(F,F)XB(F,F)—F

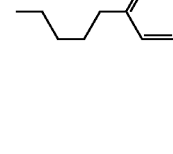

Example 2. 5-BB(F)B(F,F)XB(F,F)—F

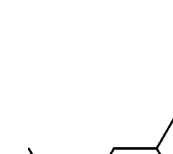

Example 3. 3-B(F)BB-5

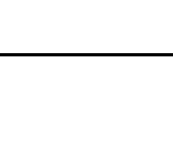

Example 4. 4-GHB(F,F)—F

Comparative Example 1

Example 5 was selected from the compositions disclosed in WO 2009/089898 A for comparison. The basis for the selection was because the composition included the second, third and forth components although it did not include the first component, and it had the largest dielectric anisotropy. The composition was prepared and measured according to the method described above for comparison under the same measurement conditions. The components and the characteristics were as follows.

| | | |
|---|---|---|
| 3-HGB(F,F)XB(F,F)-F | (3-1-6) | 15% |
| 4-HH-V | (2-1) | 4% |
| 3-HHBH-3 | (2) | 2% |
| 2-BB(F,F)XB(F,F)-F | (3-2-1) | 6% |
| 3-BB(F,F)XB(F,F)-F | (3-2-1) | 5% |
| 2-HHXB(F,F)-F | (3-3-1) | 13% |
| 3-HHXB(F,F)-F | (3-3-1) | 14% |
| 5-HHXB(F,F)-F | (3-3-1) | 13% |
| 1-HHB(F,F)-F | (4-6) | 6% |
| 2-HHB(F,F)-F | (4-6) | 8% |
| 3-HHB(F,F)-F | (4-6) | 9% |
| 5-HHB(F,F)-F | (4-6) | 5% |

NI = 78.0° C.;
Tc ≦ 0° C.;
Δn = 0.079;
Δε = 13.9.

Although Example 5 in WO 2009/089898 A disclosed that Δε=18.0 (reported value), the results measured by the method described above were Δε=13.9, which was smaller than the reported value.

Example 1

The composition of the invention was prepared. In the composition, the compound (1-1-1) and the compound (1-2-1) that were the first component were used instead of the compound (3-1-6) in Comparative Example. The components and the characteristics were as follows.

| | | |
|---|---|---|
| 5-GHB(F,F)XB(F,F)-F | (1-1-1) | 5% |
| 3-GB(F)B(F,F)XB(F,F)-F | (1-2-1) | 3% |
| 4-GB(F)B(F,F)XB(F,F)-F | (1-2-1) | 4% |
| 5-GB(F)B(F,F)XB(F,F)-F | (1-2-1) | 3% |
| 4-HH-V | (2-1) | 4% |
| 3-HHBH-3 | (2) | 2% |
| 2-BB(F,F)XB(F,F)-F | (3-2-1) | 6% |
| 3-BB(F,F)XB(F,F)-F | (3-2-1) | 5% |
| 2-HHXB(F,F)-F | (3-3-1) | 13% |
| 3-HHXB(F,F)-F | (3-3-1) | 14% |
| 5-HHXB(F,F)-F | (3-3-1) | 13% |
| 1-HHB(F,F)-F | (4-6) | 6% |
| 2-HHB(F,F)-F | (4-6) | 8% |
| 3-HHB(F,F)-F | (4-6) | 9% |
| 5-HHB(F,F)-F | (4-6) | 5% |

NI = 74.7° C.;
Tc ≦ −20° C.;
Δn = 0.082;
Δε = 16.3.

The dielectric anisotropy of this composition that included the first component was 16.3, which was larger than that of Comparative Example 1

Example 2

The following composition was prepared and measured by the method described above. The components and the characteristics were as follows.

| | | |
|---|---|---|
| 4-GB(F)B(F,F)XB(F,F)-F | (1-2-1) | 4% |
| 5-GB(F)B(F,F)XB(F,F)-F | (1-2-1) | 6% |
| 5-HH-V | (2-1) | 5% |
| 3-HH-V1 | (2-1) | 8% |
| 3-BB(F)B(F,F)XB(F,F)-F | (3-1-1) | 2% |
| 4-BB(F)B(F,F)XB(F,F)-F | (3-1-1) | 9% |
| 3-BB(F,F)XB(F,F)-F | (3-2-1) | 12% |
| 1-HHXB(F,F)-F | (3-3-1) | 8% |
| 3-HHXB(F,F)-F | (3-3-1) | 15% |
| 3-GHB(F,F)-F | (4-1) | 3% |
| 4-GHB(F,F)-F | (4-1) | 8% |
| 5-GHB(F,F)-F | (4-1) | 12% |
| 2-HHBB(F,F)-F | (4-14) | 2% |
| 3-HHBB(F,F)-F | (4-14) | 4% |
| 4-HHBB(F,F)-F | (4-14) | 2% |

NI = 75.8° C.;
Tc ≦ −30° C.;
Δn = 0.101;
Δε = 19.8;
γ1 = 211 mPa · s.

Example 3

The following composition was prepared and measured by the method described above. The components and the characteristics were as follows.

| | | |
|---|---|---|
| 4-GB(F)B(F,F)XB(F,F)-F | (1-2-1) | 4% |
| 5-GB(F)B(F,F)XB(F,F)-F | (1-2-1) | 5% |
| 5-HH-V | (2-1) | 8% |
| 3-HH-V1 | (2-1) | 8% |
| V-HHB-1 | (2-7) | 4% |
| 3-BB(F)B(F,F)XB(F,F)-F | (3-1-1) | 2% |
| 4-BB(F)B(F,F)XB(F,F)-F | (3-1-1) | 8% |
| 5-BB(F)B(F,F)XB(F,F)-F | (3-1-1) | 3% |
| 3-HGB(F,F)XB(F,F)-F | (3-1-6) | 3% |
| 4-HGB(F,F)XB(F,F)-F | (3-1-6) | 6% |
| 3-BB(F,F)XB(F,F)-F | (3-2-1) | 10% |
| 1-HHXB(F,F)-F | (3-3-1) | 6% |
| 3-HHXB(F,F)-F | (3-3-1) | 13% |
| 3-GHB(F,F)-F | (4-1) | 3% |
| 4-GHB(F,F)-F | (4-1) | 7% |
| 5-GHB(F,F)-F | (4-1) | 10% |

NI = 75.0° C.;
Tc ≦ −30° C.;
Δn = 0.100;
Δε = 19.9;
γ1 = 181 mPa · s.

Example 4

The following composition was prepared and measured by the method described above. The components and the characteristics were as follows.

| | | |
|---|---|---|
| 3-GB(F)B(F,F)XB(F,F)-F | (1-2-1) | 5% |
| 4-GB(F)B(F,F)XB(F,F)-F | (1-2-1) | 3% |
| 5-GB(F)B(F,F)XB(F,F)-F | (1-2-1) | 2% |
| 3-HH-V | (2-1) | 16% |
| 3-BB(F)B(F,F)XB(F,F)-F | (3-1-1) | 3% |
| 4-BB(F)B(F,F)XB(F,F)-F | (3-1-1) | 6% |
| 2-HGB(F,F)XB(F,F)-F | (3-1-6) | 5% |
| 3-HGB(F,F)XB(F,F)-F | (3-1-6) | 3% |
| 4-HGB(F,F)XB(F,F)-F | (3-1-6) | 2% |
| 2-BB(F,F)XB(F,F)-F | (3-2-1) | 2% |
| 3-BB(F,F)XB(F,F)-F | (3-2-1) | 6% |
| 3-HHXB(F,F)-F | (3-3-1) | 3% |
| 3-GHB(F,F)-F | (4-1) | 4% |
| 4-GHB(F,F)-F | (4-1) | 8% |
| 5-GHB(F,F)-F | (4-1) | 12% |
| 3-HHEB(F,F)-F | (4-4) | 6% |
| 5-HHEB(F,F)-F | (4-4) | 4% |
| 2-HHBB(F,F)-F | (4-14) | 2% |
| 3-HHBB(F,F)-F | (4-14) | 4% |

-continued

| | | |
|---|---|---|
| 4-HHBB(F,F)-F | (4-14) | 2% |
| 5-HHBB(F,F)-F | (4-14) | 2% |

NI = 83.0° C.;
Tc ≦ −20° C.;
Δn = 0.101;
Δε = 21.1;
γ1 = 227 mPa · s.

Example 5

The following composition was prepared and measured by the method described above. The components and the characteristics were as follows.

| | | |
|---|---|---|
| V2-GB(F)B(F,F)XB(F,F)-F | (1-2-1) | 5% |
| 2-HH-3 | (2-1) | 5% |
| 3-HH-V | (2-1) | 10% |
| VFF-HH-3 | (2-1) | 5% |
| 3-HB-O2 | (2-2) | 2% |
| 5-HBB(F)B-2 | (2-14) | 5% |
| 3-BB(F)B(F,F)XB(F,F)-F | (3-1-1) | 3% |
| 4-BB(F)B(F,F)XB(F,F)-F | (3-1-1) | 8% |
| 5-BB(F)B(F,F)XB(F,F)-F | (3-1-1) | 9% |
| 4-HBBXB(F,F)-F | (3-1-2) | 3% |
| 3-BB(F,F)XB(F,F)-F | (3-2-1) | 16% |
| V2-BB(F,F)XB(F,F)-F | (3-2-1) | 4% |
| 3-HHXB(F,F)-F | (3-3-1) | 9% |
| 3-HHEB(F,F)-F | (4-4) | 7% |
| 3-HBEB(F,F)-F | (4-5) | 3% |
| 4-HBEB(F,F)-F | (4-5) | 3% |
| 5-HBEB(F,F)-F | (4-5) | 3% |

NI = 72.5° C.;
Tc ≦ −30° C.;
Δn = 0.119;
Δε = 19.2.

Example 6

The following composition was prepared and measured by the method described above. The components and the characteristics were as follows.

| | | |
|---|---|---|
| 4-GB(F)B(F,F)XB(F,F)-F | (1-2-1) | 4% |
| 3-GB(F)B(F,F)XB(F)-OCF3 | (1-2-3) | 2% |
| 3-HH-V | (2-1) | 17% |
| 1-BB-2V | (2-3) | 2% |
| 3-HHB-1 | (2-7) | 3% |
| 3-HHB-O1 | (2-7) | 2% |
| 2-BB(F)B-3 | (2-9) | 2% |
| 3-HB(F)HH-5 | (2-15) | 3% |
| 3-BB(F)B(F,F)XB(F,F)-F | (3-1-1) | 3% |
| 4-BB(F)B(F,F)XB(F,F)-F | (3-1-1) | 10% |
| 5-BB(F)B(F,F)XB(F,F)-F | (3-1-1) | 10% |
| 3-BB(F,F)XB(F,F)-F | (3-2-1) | 15% |
| 3-HHXB(F,F)-F | (3-3-1) | 9% |
| 3-HHEB(F,F)-F | (4-4) | 3% |
| 3-HBEB(F,F)-F | (4-5) | 3% |
| 4-HBEB(F,F)-F | (4-5) | 3% |
| 5-HBEB(F,F)-F | (4-5) | 3% |
| V-HHB(F,F)-F | (4-6) | 2% |
| 3-H2HB(F,F)-F | (4-7) | 2% |
| 3-HBB(F,F)-F | (4-9) | 2% |

NI = 79.6° C.;
Tc ≦ −20° C.;
Δn = 0.127;
Δε = 18.0.

Example 7

The following composition was prepared and measured by the method described above. The components and the characteristics were as follows.

| | | |
|---|---|---|
| 5-GHB(F,F)XB(F,F)-F | (1-1-1) | 2% |
| 4-GB(F)B(F,F)XB(F,F)-F | (1-2-1) | 3% |
| 5-GB(F)B(F,F)XB(F,F)-F | (1-2-1) | 2% |
| 5-HH-V | (2-1) | 15% |
| 3-HHEBH-3 | (2-11) | 4% |
| 3-HHEBH-4 | (2-11) | 3% |
| 3-HHEBH-5 | (2-11) | 3% |
| 3-BB(F)B(F,F)XB(F,F)-F | (3-1-1) | 3% |
| 4-BB(F)B(F,F)XB(F,F)-F | (3-1-1) | 9% |
| 5-BB(F)B(F,F)XB(F,F)-F | (3-1-1) | 5% |
| 2-BB(F,F)XB(F,F)-F | (3-2-1) | 3% |
| 3-BB(F,F)XB(F,F)-F | (3-2-1) | 18% |
| 3-BB(F,F)XB(F)-OCF3 | (3-2-3) | 8% |
| 1-HHXB(F,F)-F | (3-3-1) | 8% |
| 3-HHXB(F,F)-F | (3-3-1) | 14% |

NI = 83.5° C.;
Tc ≦ −30° C.;
Δn = 0.115;
Δε = 18.4.

The compositions in Examples 1 to 7 had a large dielectric anisotropy in comparison with that in Comparative Example 1. Thus, the liquid crystal composition of the invention was so much superior in characteristics.

INDUSTRIAL APPLICABILITY

The invention provides a liquid crystal composition that satisfies at least one of characteristics such as a high maximum temperature of a nematic phase, a low minimum temperature of a nematic phase, a small viscosity, a suitable optical anisotropy, a large dielectric anisotropy, a large specific resistance, a large elastic constant, a high stability to ultraviolet light and a high stability to heat, or that is suitably balanced regarding at least two of the characteristics. Since a liquid crystal display device that contains the composition provides an AM device having a short response time, a large voltage holding ratio, a large contrast ratio, a long service life and so forth, it can be used for a liquid crystal projector, a liquid crystal television and so forth.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A liquid crystal composition that has a nematic phase and comprises three components, wherein a first component is at least one compound selected from the group of compounds represented by formula (1), a second component is at least one compound selected from the group of compounds represented by formula (2), and a third component is at least one compound selected from the group of compounds represented by formula (3-1) to formula (3-3) and at least one compound selected from the group of compounds represented by formula (3-1-2):

(1)

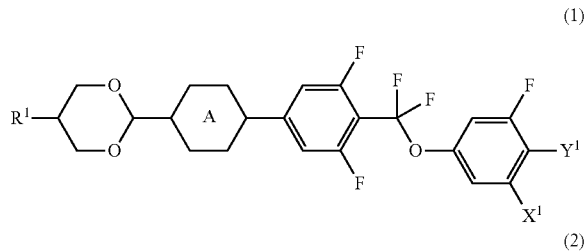

(2)

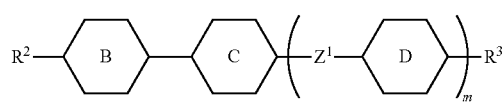

(3-1)

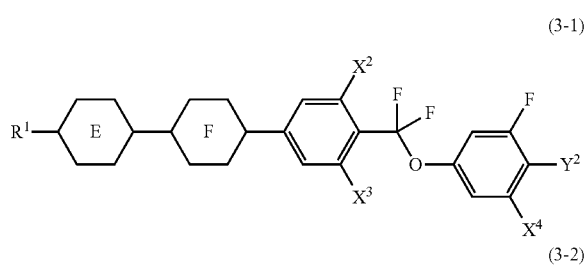

(3-2)

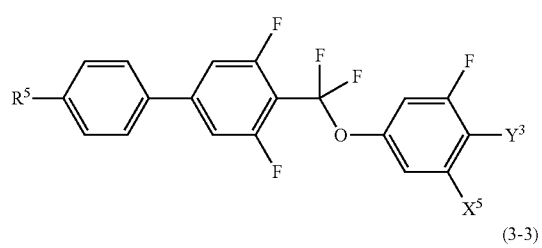

(3-3)

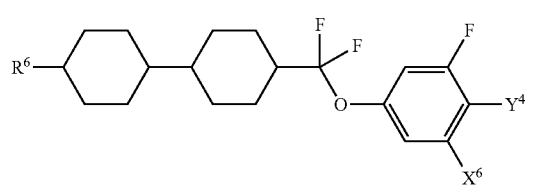

(3-1-2)

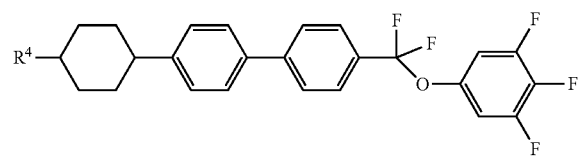

wherein $R^1$ is alkyl having 1 to 12 carbons or alkenyl having 2 to 12 carbons; $R^2$ is alkyl having 1 to 12 carbons, alkenyl having 2 to 12 carbons, or alkenyl having 2 to 12 carbons in which hydrogen is replaced by fluorine; $R^3$ is alkyl having 1 to 12 carbons, alkoxy having 1 to 12 carbons, alkoxymethyl having 2 to 12 carbons or alkenyl having 2 to 12 carbons; $R^4$, $R^5$ and $R^6$ are each independently alkyl having 1 to 12 carbons or alkenyl having 2 to 12 carbons; the ring A, the ring B, the ring C and the ring D are each independently 1,4-cyclohexylene, 1,4-phenylene, 2-fluoro-1,4-phenylene, 3-fluoro-1,4-phenylene, 3,5-difluoro-1,4-phenylene, 2,5-difluoro-1,4-phenylene or tetrahydropyran-2,5-diyl; the ring E is 1,4-cyclohexylene, 1,4-phenylene, 2-fluoro-1,4-phenylene, 3-fluoro-1,4-phenylene, 3,5-difluoro-1,4-phenylene or tetrahydropyran-2,5-diyl; the ring F is 1,4-cyclohexylene, 1,4-phenylene, 2-fluoro-1,4-phenylene, 3-fluoro-1,4-phenylene, 3,5-difluoro-1,4-phenylene, 1,3-dioxane-2,5-diyl or tetrahydropyran-2,5-diyl; $X^1$ is hydrogen or fluorine; $X^2$, $X^3$, $X^4$, $X^5$ and $X^6$ are each independently hydrogen or fluorine; $Y^1$ is fluorine, chlorine or trifluoromethoxy; $Y^2$, $Y^3$ and $Y^4$ are each independently fluorine, chlorine or trifluoromethoxy; $Z^1$ is independently a single bond, ethylene or carbonyloxy; and m is 0, 1 or 2.

2. The liquid crystal composition according to claim 1, further comprising at least one compound selected from the group of compounds represented by formula (4) as a fourth component:

(4)

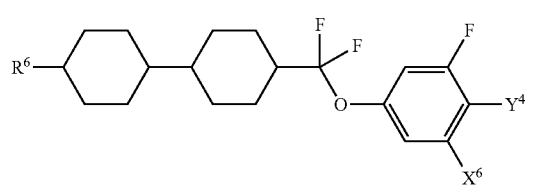

wherein $R^7$ is alkyl having 1 to 12 carbons or alkenyl having 2 to 12 carbons; the ring G is independently 1,4-cyclohexylene, 1,4-phenylene, 2-fluoro-1,4-phenylene, 3-fluoro-1,4-phenylene, 3,5-difluoro-1,4-phenylene, 1,3-dioxane-2,5-diyl or tetrahydropyran-2,5-diyl; $X^7$ is hydrogen or fluorine; $Y^5$ is fluorine, chlorine or trifluoromethoxy; $Z^2$ is independently a single bond, ethylene or carbonyloxy; and n is 1, 2 or 3.

3. The liquid crystal composition according claim 1, wherein the first component is at least one compound selected from the group of compounds represented by formula (1-1-1), formula (1-2-1) and formula (1-3-1):

(1-1-1)

(1-2-1)

(1-3-1)

wherein $R^1$ is alkyl having 1 to 12 carbons or alkenyl having 2 to 12 carbons.

4. The liquid crystal composition according to claim 1, wherein the second component is at least one compound selected from the group of compounds represented by formula (2-1):

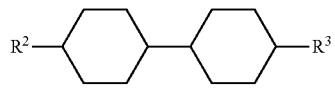
(2-1)

wherein $R^2$ is alkyl having 1 to 12 carbons, alkenyl having 2 to 12 carbons, or alkenyl having 2 to 12 carbons in which hydrogen is replaced by fluorine; and $R^3$ is alkyl having 1 to 12 carbons, alkoxy having 1 to 12 carbons, alkoxymethyl having 2 to 12 carbons or alkenyl having 2 to 12 carbons.

5. The liquid crystal composition according to claim 1, wherein the third component is at least one compound selected from the group of compounds represented by formula (3-1-1), formula (3-1-3), formula (3-2-1) and formula (3-3-1):

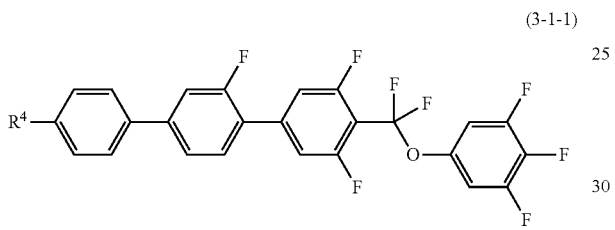
(3-1-1)

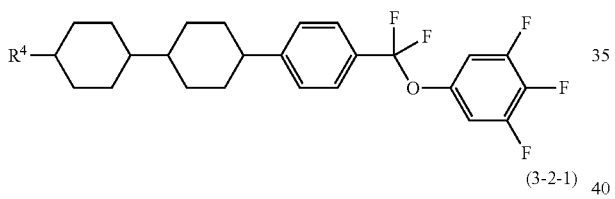
(3-1-3)

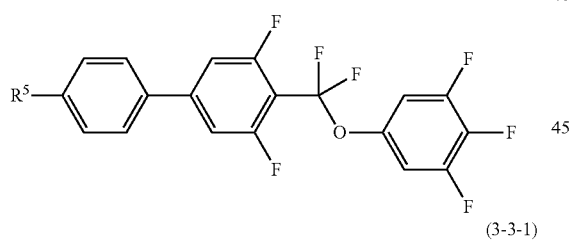
(3-2-1)

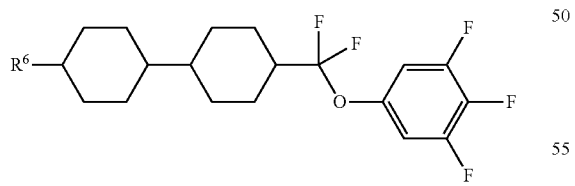
(3-3-1)

wherein $R^4$, $R^5$ and $R^6$ are each independently alkyl having 1 to 12 carbons or alkenyl having 2 to 12 carbons.

6. The liquid crystal composition according to claim 5, wherein the third component is at least one compound selected from the group of compounds represented by formula (3-1-1), formula (3-1-3).

7. The liquid crystal composition according claim 2, wherein the fourth component is at least one compound selected from the group of compounds represented by formula (4-1) to formula (4-11):

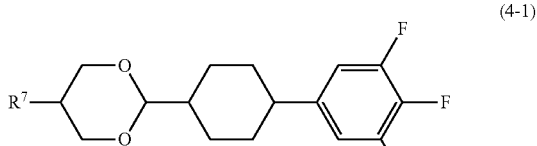
(4-1)

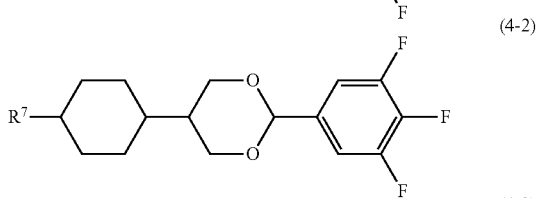
(4-2)

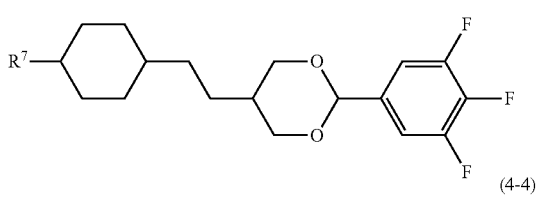
(4-3)

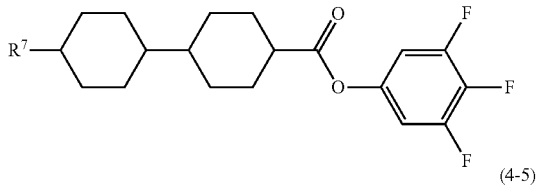
(4-4)

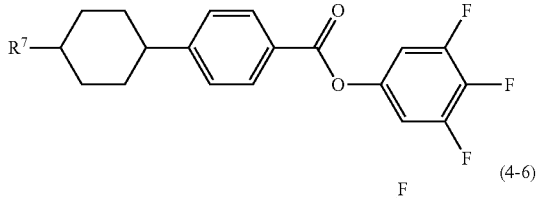
(4-5)

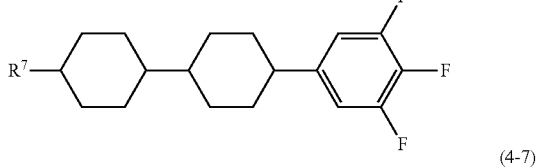
(4-6)

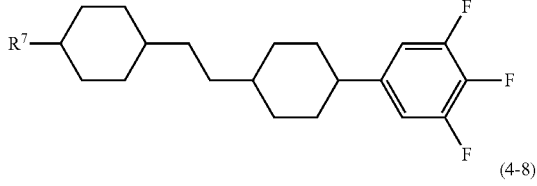
(4-7)

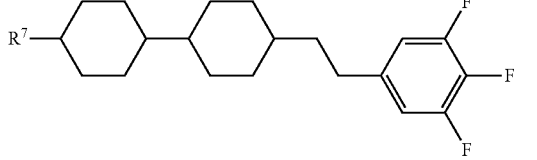
(4-8)

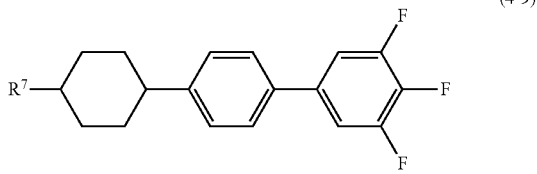
(4-9)

-continued

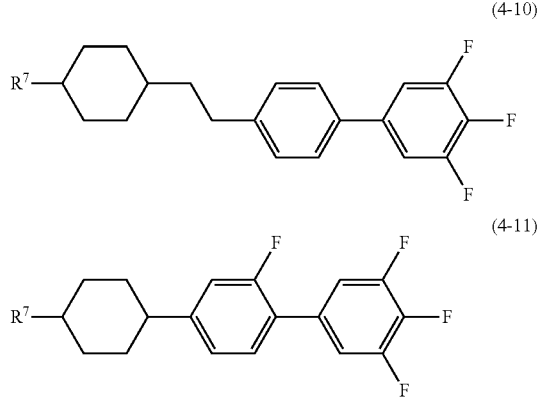

(4-10)

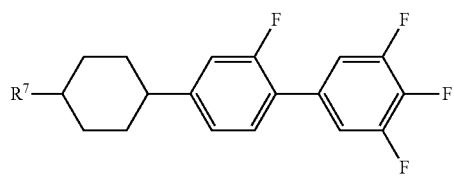

(4-11)

wherein $R^7$ is alkyl having 1 to 12 carbons or alkenyl having 2 to 12 carbons.

8. The liquid crystal composition according to claim 1, wherein the ratio of the first component is in the range of approximately 5% to approximately 30% by weight, the ratio of the second component is in the range of approximately 5% to approximately 40% by weight, and the ratio of the third component is in the range of approximately 5% to approximately 70% by weight based on the total weight of the liquid crystal composition.

9. A liquid crystal display device containing the liquid crystal composition according to claim 1.

10. The liquid crystal display device according to claim 9, wherein an operating mode of the liquid crystal display device is a TN mode, an OCB mode, an IPS mode, a FFS mode or a PSA mode, and a driving mode of the liquid crystal display device is an active matrix mode.

* * * * *